United States Patent
Bartlett et al.

(10) Patent No.: US 11,324,865 B2
(45) Date of Patent: May 10, 2022

(54) VIBRATORY WAVEFORM FOR BREAST PUMP

(71) Applicant: LANSINOH LABORATORIES, INC., Alexandria, VA (US)

(72) Inventors: Rush Bartlett, Alexandria, VA (US); Frank Tinghwa Wang, Alexandria, VA (US)

(73) Assignee: Lansinoh Laboratories, Inc., Alexandria, VA (US)

( * ) Notice: Subject to any disclaimer, the term of this patent is extended or adjusted under 35 U.S.C. 154(b) by 0 days.

(21) Appl. No.: 17/244,517

(22) Filed: Apr. 29, 2021

(65) Prior Publication Data

US 2021/0244864 A1     Aug. 12, 2021

Related U.S. Application Data

(60) Division of application No. 17/090,250, filed on Nov. 5, 2020, now Pat. No. 11,097,038, which is a
(Continued)

(51) Int. Cl.
*A61M 1/06*     (2006.01)
*A61M 1/00*     (2006.01)

(52) U.S. Cl.
CPC .............. *A61M 1/06* (2013.01); *A61M 1/74* (2021.05); *A61M 1/815* (2021.05); *A61M 1/062* (2014.02);
(Continued)

(58) Field of Classification Search
CPC .... A61M 1/06; A61M 1/0697; A61M 1/0693; A61M 2210/1007
See application file for complete search history.

(56) References Cited

U.S. PATENT DOCUMENTS 2,301,781 A    11/1942   Higbee
4,673,388 A *   6/1987   Schlensog ............. A61M 1/782
                                                      604/74
(Continued)

FOREIGN PATENT DOCUMENTS

CN         2880094 Y     3/2007
CN         1958084 A     5/2007
(Continued)

OTHER PUBLICATIONS

Declaration of Rush Bartlett: Exhibit A, "Instructions for Use Spectra S1 Plus / S2 Plus", 16 pages, from the Internet: <https://images-na.ssl-images-amazon.com/images/I/A119ueCmeLS.pdf>, document created Jun. 13, 2017.
(Continued)

*Primary Examiner* — Nathan R Price
*Assistant Examiner* — Melissa A Snyder
(74) *Attorney, Agent, or Firm* — Merchant & Gould P.C.

(57) ABSTRACT

A method for facilitating milk extraction from a female breast may involve applying a breast contacting portion of a breast pump system to a breast, activating the breast pump system to administer multiple breast pumping cycles, and applying vibrations to the breast during at least a portion of each of the breast pumping cycles, using a vibration device. A vibration generating device may be a component of a breast pump system, an added attachment on a breast pump system or a separate component that works in conjunction with a breast pump system.

9 Claims, 18 Drawing Sheets

Related U.S. Application Data continuation of application No. PCT/US2019/049946, filed on Sep. 6, 2019.

(60) Provisional application No. 62/727,909, filed on Sep. 6, 2018.

(52) U.S. Cl.
CPC . *A61M 2205/33* (2013.01); *A61M 2210/1007* (2013.01)

(56) References Cited

U.S. PATENT DOCUMENTS

| | | | |
|---|---|---|---|
| 4,740,196 A | 4/1988 | Powell | |
| 5,656,026 A | 8/1997 | Joseph | |
| 7,294,120 B1 | 11/2007 | Eidsen et al. | |
| 8,444,596 B2 | 5/2013 | Paterson et al. | |
| 8,545,438 B2 | 10/2013 | Kazazoglu et al. | |
| 8,715,225 B2 | 5/2014 | Hegen | |
| 8,961,454 B2 | 2/2015 | Chen | |
| 9,539,376 B2 | 1/2017 | Makower et al. | |
| 9,539,377 B2 | 1/2017 | Makower et al. | |
| 9,616,156 B2 | 4/2017 | Alvarez et al. | |
| D809,646 S | 2/2018 | Mason et al. | |
| D811,579 S | 2/2018 | Chang et al. | |
| D828,542 S | 9/2018 | Mason et al. | |
| 10,105,474 B2 | 10/2018 | Barral et al. | |
| D832,995 S | 11/2018 | Mason et al. | |
| D834,177 S | 11/2018 | Chang et al. | |
| 10,279,091 B1 | 5/2019 | Jones | |
| 10,617,806 B2 | 4/2020 | Bartlett et al. | |
| 10,857,271 B2 | 12/2020 | Bartlett et al. | |
| 2005/0234400 A1 | 10/2005 | Onuki et al. | |
| 2007/0179439 A1 | 8/2007 | Vogelin et al. | |
| 2014/0031744 A1 | 1/2014 | Chen | |
| 2015/0065994 A1 | 3/2015 | Fridman et al. | |
| 2016/0038662 A1 | 2/2016 | Felber | |
| 2016/0100888 A1 | 4/2016 | Ferrari | |
| 2016/0287767 A1 | 10/2016 | Simmons et al. | |
| 2016/0296681 A1 | 10/2016 | Gaskin et al. | |
| 2017/0065753 A1 | 3/2017 | Nowroozi et al. | |
| 2017/0072118 A1 | 3/2017 | Makower et al. | |
| 2017/0182231 A1 | 6/2017 | Aalders et al. | |
| 2018/0093024 A1 | 4/2018 | Analytis et al. | |
| 2018/0110906 A1 | 4/2018 | Barack | |
| 2018/0193559 A1 | 7/2018 | Hirata et al. | |
| 2018/0361040 A1 | 12/2018 | O'Toole et al. | |
| 2018/0369464 A1 | 12/2018 | Aalders et al. | |
| 2020/0016305 A1 | 1/2020 | Weinberg | |
| 2020/0078502 A1 | 3/2020 | Bartlett et al. | |
| 2020/0230305 A1 | 7/2020 | Bartlett et al. | |
| 2021/0085842 A1 | 3/2021 | Bartlett et al. | |

FOREIGN PATENT DOCUMENTS

| | | |
|---|---|---|
| CN | 105749366 A | 7/2016 |
| CN | 109010963 A | 12/2018 |
| CN | 110251750 A | 9/2019 |
| CN | 108939328 B | 5/2020 |
| EP | 3299043 A1 | 3/2018 |
| RU | 190862 U1 | 7/2019 |
| WO | 2012037848 A1 | 3/2012 |
| WO | 2016014469 A1 | 1/2016 |
| WO | 2016014488 A1 | 1/2016 |
| WO | 2017108555 A1 | 6/2017 |

OTHER PUBLICATIONS

Declaration of Rush Bartlett, 10 pages, dated Nov. 4, 2020.

Declaration of Rush Bartlett: Exhibit B, Part I, Waveform Parameters Observed in the Spectra S1 pump, 252 pages, dated Nov. 4, 2020.

Declaration of Rush Bartlett: Exhibit B, Part 2, Waveform Parameters Observed in the Spectra S9 pump, 193 pages, dated Nov. 4, 2020.

"Elvie Pump" Elvie.com [online]. Retrieved from the Internet: <URL: https://www.elvie.com/shop/elvie-pump>, 12 pages. Retrieved on Sep. 3, 2019.

Kent et al., "Importance of Vacuum for Breastmilk Expression," Breastfeed. Med., 3(1):11-19, Mar. 2008.

"Medela Launches SonataTM Nationwide and Redefines the Breast Pump," Medelabreastfeedingus.com [online] Retrieved from the Internet: <URL: http://www.medelabreastfeedingus.com/media-center/271/medela-launches-sonata-nationwide-and-redefin>, 4 pages, Jan. 3, 2017.

Mitoulas et al., "Effect of vacuum Profile on Breast Milk Expression Using an Electric Breast Pump," J. Hum. Lact. 18(4): 353-360, Nov. 2002.

Sumiko et al, 変動リズムを含む吸引によるさく乳の特徴(第1報) 排乳量の時間的変化と 母親使用感(会議録) [Study of Breast Pump Suction with Variable Rhythm Temporal Change in Breast Milk Flow and Mothers' Feelings] Japanese Journal of Maternal Health, 59(3):247, 2018 [Poster with English annotations].

International Search Report and Written Opinion in PCT/US2019/049946, dated Dec. 5, 2019, 15 pages.

\* cited by examiner

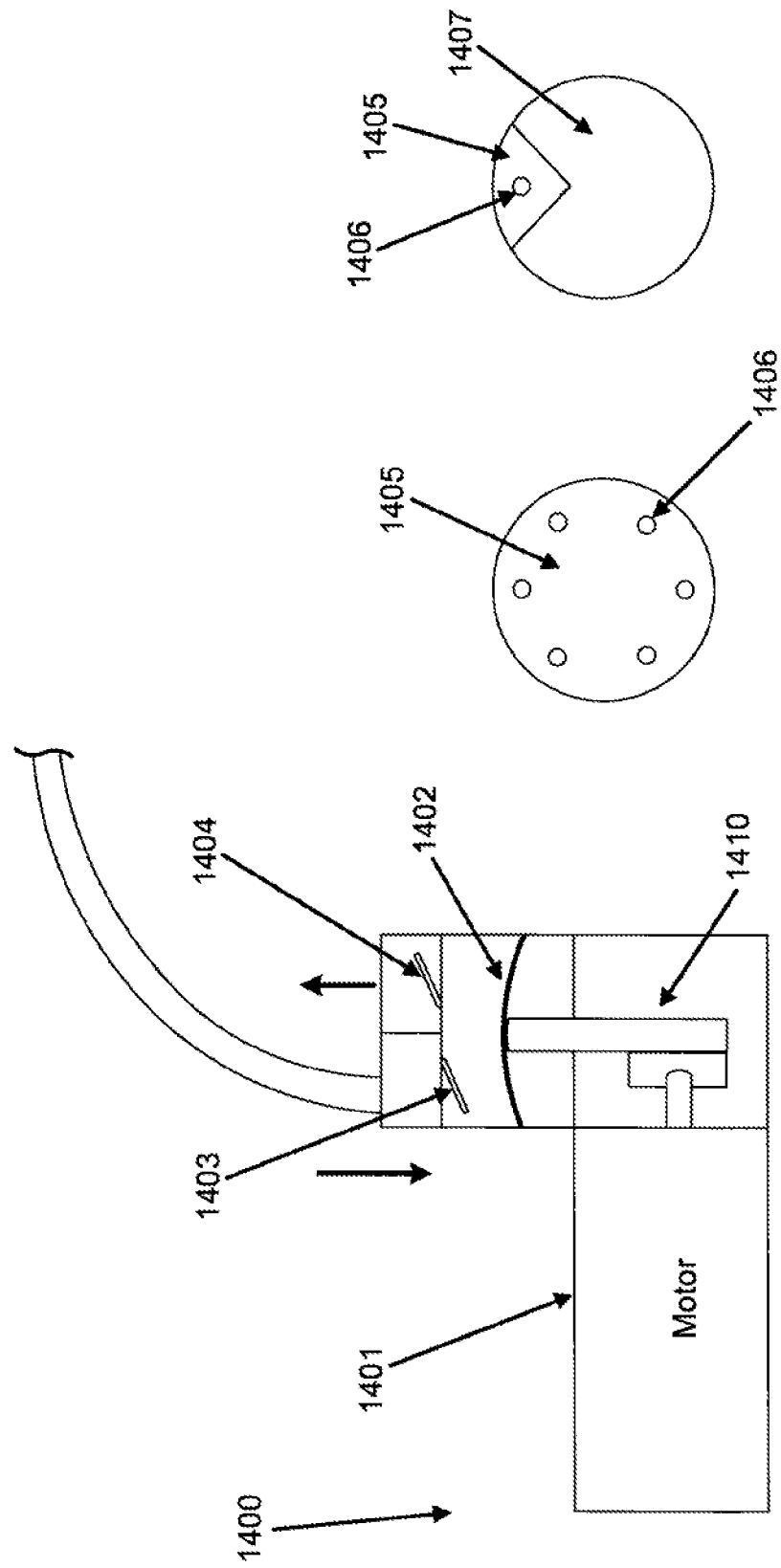

VIBRATORY WAVEFORM FOR BREAST PUMP

CROSS-REFERENCE TO RELATED APPLICATIONS

This application is a divisional of U.S. patent application Ser. No. 17/090,250, filed Nov. 5, 2020, which is a continuation of PCT International Patent Application No. PCT/US2019/049946, filed Sep. 6, 2019, which claims priority to U.S. Provisional Patent Application No. 62/727,909, filed Sep. 6, 2018, the disclosures of which are hereby incorporated by reference herein in their entireties. To the extent appropriate, a claim of priority is made to each of the above disclosed applications.

This application is related to U.S. patent application Ser. No. 16/563,211, filed Sep. 6, 2019, now U.S. Pat. No. 10,617,806, which claims priority to U.S. Provisional Patent Application No. 62/727,909, filed Sep. 6, 2018.

FIELD

The present application is directed to devices, systems and methods for facilitating the collection of breast milk.

BACKGROUND

Breastfeeding is the recommended method to provide nutrients to a newborn child for the first year of life. Many mothers, however, return to work soon after giving birth, have difficulty breastfeeding their newborns, or have challenges breastfeeding for other reasons. As a result, many mothers rely on breast pumping to express their breast milk and use bottles to feed their newborns. Since a mother might need to pump as often as eight times a day to maintain her milk supply and/or prevent breast engorgement, it is essential that each breast pumping session be as efficient as possible—i.e., emptying as much milk from the breast as possible, in the shortest amount of time.

Breast pumps operate by applying a suction on the breast for a short period of time, during which a small amount of milk is expressed. The breast pump then releases the suction and repeats the cycle of on suction/off suction until the breast is empty. The amount of vacuum applied to the breast during one cycle of on suction/off suction, referred to as a waveform, is controlled by the breast pump by adjusting the applied voltage and/or current to an internal vacuum motor and solenoid, to mimic the baby feeding on the breast. Typical breast pumps allow the mother to adjust the cycle speed and the amount of suction, in an attempt to maximize efficiency of the pump. It is still often challenging, however, to adjust a breast pump to work efficiently.

Therefore, it would be ideal to have a breast pump that worked efficiently to prevent breast engorgement. Ideally, such a breast pump would empty as much milk from the breast as possible, in a short amount of time. Additionally, such a breast pump would also ideally be easy to adjust for an individual woman's specific needs. At least some of these objectives are addressed by the following disclosure.

SUMMARY

This application describes an improved breast pump device and method that allows for increased milk volume flow rates and/or increased pump efficiency. The device and method involve applying vibrations to the breast during the breast pump cycle (or "waveform"), to increase the volume flow rate of expressed milk for a given cycle speed and suction level. The breast pump waveform with added vibrations according to the present disclosure is often referred to herein as a "vibratory waveform." The vibratory waveform helps the breast pump empty milk from the breast more completely and/or in a shorter time than would occur from simply adjusting the breast pump's cycle speed and/or suction level. Creating a vibratory waveform may also reduce the time to letdown, the reflex that leads to the release of breast milk. In any given pumping method example, the vibratory waveform may be applied, and the pump's cycle speed and/or suction level may also be adjusted. Alternatively, the vibratory waveform may be applied (and have advantageous results) without any adjustment of cycle speed or suction level.

In various embodiments, the breast pump applies vibration to the breast through small oscillations in the suction pattern as the vacuum is reduced, held, and/or released, as part of the pump cycle. The vibrations may facilitate improved letdown and reduce the shear stress of milk against the inner walls of the milk ducts, to help increase the volume flow rate of milk flowing out of the milk duct. The vibration feeling is most pronounced when the suction is increased and decreased in a rapid cyclical manner.

The vibratory waveform can be generated in a breast pump system using a variety of devices and methods. In some embodiments, a vibratory device is added to a breast pump device. Alternatively, one or more components of a breast pump device may be altered or adjusted to cause vibrations. In other embodiments, a separate device may be used to generate vibrations. Examples of these types of embodiments include but are not limited to modulating the vacuum pump of a breast pump device, modulating the solenoid of a breast pump device, or adding a vibratory motor, a piezoelectric element, a speaker, a shaking element on the bottom of the pump motor housing or pump, an off-center rotary weight on the motor or shaft, or teeth in the wall of the piston housing that allow the diaphragm to "chatter" forward and backward. The vibration source can be built into the pump, the flange or an external device.

In one aspect of the present disclosure, a method for facilitating milk extraction from a female breast may involve applying a breast contacting portion of a breast pump system to a breast, activating the breast pump system to administer multiple breast pumping cycles, and applying vibrations to the breast during at least a portion of each of the breast pumping cycles, using a vibration device. In some embodiments, each of the breast pumping cycles may include an increasing vacuum segment, during which an amount of the vacuum force applied to the breast increases, and a decreasing vacuum segment, during which the amount of the vacuum force applied to the breast decreases.

Optionally, each of the breast pumping cycles may further include at least one vacuum hold segment, during which the amount of the vacuum force applied to the breast is held constant. For example, a vacuum hold segment may be a maximum vacuum force hold segment occurring after the increasing vacuum segment, during which the amount of the vacuum force is kept constant at a maximum vacuum force, or a minimum vacuum force hold segment occurring after the decreasing vacuum segment, during which the amount of the vacuum force is kept constant at a minimum vacuum force. Vibrations may be applied to any segment (or multiple segments) of the breast pumping cycle, including the increasing vacuum segment, the decreasing vacuum segment, and/or the vacuum hold segment(s). In some embodiments, the vibrations may be applied to the breast during an entire length of each cycle.

According to various embodiments, the applied vibrations may have a frequency of between 0 Hz and 10 MHz. More ideally, the vibrations may have a frequency of 5-10 Hz in some embodiments. According to various embodiments, the vibrations may be applied in a pattern, such as but not limited to a stair-step pattern, a wavy pattern or an oscillating pattern.

In some embodiments, the vibration device that generates the vibrations in the breast is part of the breast pump system. Alternatively, the vibration device may be a separate device that is not directly connected to the breast pump system and that contacts the breast separately from the breast contacting portion of the breast pump system. For example, applying the vibrations may involve activating a motor and/or a solenoid that that is/are part of the vibration device. In some embodiments, applying the vibrations may involve applying an additional vacuum force via the breast pump system and releasing the additional vacuum force. For example, applying and releasing the additional vacuum force may involve driving air in an opposite direction through one or more holes in a one-way valve that is part of the breast pump system.

In some embodiments, the step of applying the vibrations is activated by a control unit of the breast pump system. Alternatively or additionally, applying the vibrations may be activated by a user of the breast pump system. Optionally, the method may further include adjusting the application of the vibrations. The adjusting may be performed by a control unit of the breast pump system and/or by a user, in various embodiments.

In another aspect of the present disclosure, a device for facilitating milk extraction from a female breast may include a housing and a vibration generating device coupled with the housing for creating vibrations in a breast to facilitate milk extraction from the breast. The device may be attached to, or incorporated into, a breast pump device. Alternatively, the device may be a separate device, used along with a breast pump device.

In some embodiments, the vibration generating device may be a motor. In some embodiments, the device is configured to directly contact the breast at a location apart from a breast pump device. Such a device may further include an adhesive surface on the housing for temporarily attaching the housing to the breast. The device may also optionally include a wireless module in the housing for transmitting signals to and/or receiving signals from a breast pump system.

In another aspect of the present disclosure, a system for facilitating milk extraction from a female breast may include a breast pump device and a vibration generating device. The breast pump device includes a breast contacting portion, a control unit with a vacuum source, and a connector for transmitting vacuum force from the vacuum source of the control unit to the breast contacting portion. The vibration generating device is coupled with the breast pump device for creating vibrations in a breast to facilitate milk extraction from the breast.

In some embodiments, the vibration generating device is attached to the breast contacting portion. In some embodiments, the vibration generating device is part of the control unit. In some embodiments, the vibration generating device is physically separate from the breast pump device and communicates with the breast pump device via wired or wireless communication. Different types of vibration generating devices include, but are not limited to, a motor, a stepper motor, a solenoid, a one-way valve with at least one hole, a piston, a weighted portion, and a software program in the control unit containing instructions to turn the vacuum force on and off. In some embodiments, the system may further include a controller for allowing a user of the system to adjust at least one parameter of the vibrations.

The control unit may include a number of different components, such as at least one motor, at least one solenoid, and electronics configured to control the motor and the solenoid. Some embodiments may include a first motor for providing the vacuum force to the breast contacting portion and a second motor for driving air into the breast contacting portion to generate the vibrations. In this example, the second motor is the vibration generating device. Some embodiments may include a flexible bulb coupled with the second motor, where the second motor squeezes and releases the flexible bulb to push air into and pull air out of the breast contacting portion.

These and other aspects and embodiments are described in greater detail below, in reference to the attached drawing figures.

BRIEF DESCRIPTION OF THE DRAWINGS

FIG. 15A is a side view of a vacuum motor device for providing a vibratory waveform to a breast pump, according to one embodiment;

FIG. 15B is a top view of a diaphragm of a one-way valve of the motor device of FIG. 15A, including multiple holes and with the flap of the valve removed to show the diaphragm;

FIG. 15C is a top view of the diaphragm of FIG. 15B, with the flap of the valve overlying the diaphragm and including a cutout portion to expose part of the diaphragm and one of the holes;

DETAILED DESCRIPTION

Figure 1:
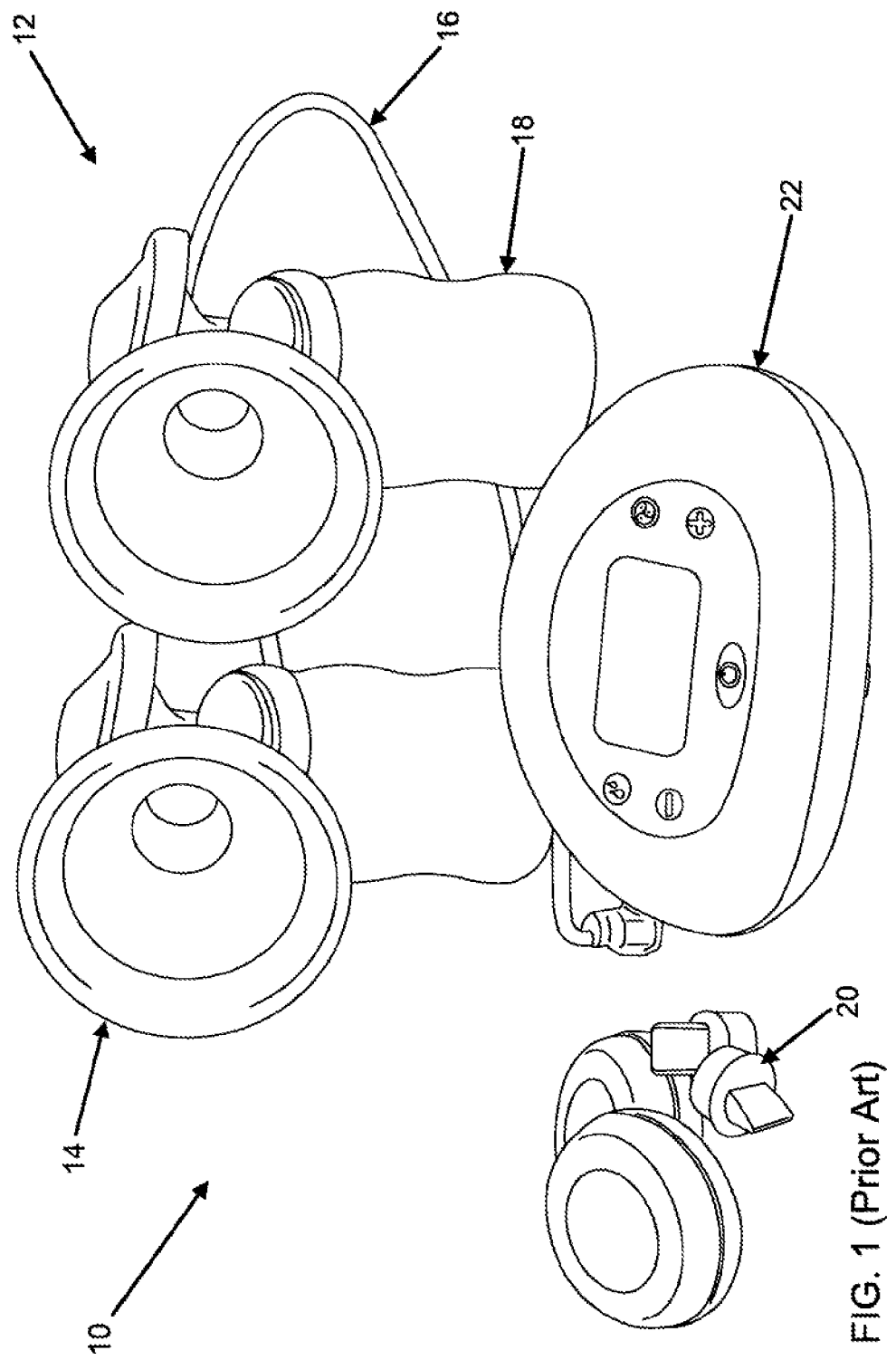
FIG. 1 is a perspective view of a currently available electric breast pump system.

Referring to FIG. 1, one example of a currently available electric breast pump system 10 is shown. In this example, the system 10 includes a breast contacting portion 12 and a control unit 22. The breast contacting portion 12 typically includes two funnels 14 (or "shields") for directly contacting and fitting partially over a woman's breasts, two milk collection receptacles 18 connected to the funnels 14, two duckbill valves 20 (or "membranes") that reside inside the breast contacting portion 12 when in use, and a tube connector 16 for connecting the funnels 14 with the control unit 22. The control unit 22 typically includes several primary components, all of which are inside the housing of the control unit 22 and thus not visible in FIG. 1. For example, the control unit 22 typically houses a vacuum motor for generating vacuum (or "suction") force that is conveyed through the tube connector 16 to the funnels 14, a solenoid that helps release vacuum pressure from the system 10, and electronics for driving the system 10.

Different terminology is sometimes used by people of skill in the art to refer to the various parts of a breast pump system 10. For example, the breast contacting portion 12 may be referred to as a "milk extraction set" or a "disposable portion," the funnels 14 are often referred to as "breast shields," and the control unit is sometimes simply referred to as "the pump." This application will typically use terminology as described immediately above, but these terms may in some cases be synonymous with other terms commonly used in the art. Therefore, the choice of terminology used to describe known components of a breast pump system or device should not be interpreted as limiting the scope of the invention as defined by the claims.

As mentioned in the Background section, currently available electric breast pump systems, such as the system 10 of FIG. 1, operate by applying vacuum force to the breast and releasing the vacuum force repeatedly during a pumping session. Each application and release of vacuum is referred to herein as one "cycle," where each cycle begins as vacuum force starts to be applied and ends right before vacuum starts to be applied again. The pattern created on a graph of pressure versus time by an operating breast pump may be referred to herein as a "pumping waveform."

Currently available breast pumps do not vibrate or generate vibrations in the breast as part of their regular function. Instead, they provide smooth, vibration-free suction and release cycles. In general, the methods described herein use one or more mechanisms to add vibrations to at least part of the breast pump cycle, in order to enhance the function of the breast pump and thus facilitate milk extraction from the breast. The application sometimes refers to the pumping waveform with the addition of vibrations as a "vibration waveform." In other words, the "vibration waveform" may refer to any breast pumping waveform that has vibrations added to it.

Current breast pumps allow for changing the cycle speed and the suction pressure of the pump. The Hagen-Poiseuille fluid dynamic equation, derived from the approximation of a Newtonian fluid undergoing laminar flow, reads as follows: $\Delta P=(8\ \mu LQ)/(\pi R^4)$, where $\Delta P$=pressure difference (in the milk duct), L is length (of the milk duct), $\mu$=dynamic viscosity (of the milk), Q=volumetric flow rate, and R=radius (of the milk duct). Current pumps only target $\Delta P$ by adjusting the suction pressure. Milk and colostrum can be approximated as a Newtonian fluid, and the dimension of the radius of the milk duct pipes can also enable us to be reasonably certain that almost all flow regimes encountered would consist of laminar flow segments. As a result, a Hagen-Poiseuille derivation from the shear stress equation $\tau=-\mu^*(dv/dr)$, where $\mu$=viscosity, v=velocity of the fluid, and r=the position along the radius in the tube, should represent a reasonable approximation. As such, the cycle speed of a breast pump affects how many suction and release cycles the breast pump operates in a minute but does not affect the volume flow rate during a cycle.

The devices, systems and methods described in this application enhance breast pump function by applying vibrations to reduce shear stress $\tau$ along a given radius of breast milk duct (or "conduit"), so that more volume in the duct will move at a higher velocity. The applied vibrations increase Q (volumetric flow rate) when other parameters are fixed, and they may also stimulate the breast to induce letdown and further increase the radial dimension R of the breast milk duct along critical flow restriction points. The decrease in $\mu$ from vibration may also be explained by the following equation, $F=\mu A\ (v/y)$. With vibration, the friction between the fluid and the walls of the duct is decreased, thereby reducing the amount of force needed to maintain the flow velocity. In addition, or as a separate effect, vibration may stimulate letdown, which increases the cross-sectional area of each milk duct. Going back to the Hagen-Poiseuille fluid dynamic equation, given a fixed $\Delta P$, $\mu$ must decrease and Q must increase to balance the equation. Letdown induces an increased radius and corresponding increase in Q, assuming the same pressure gradient.

The devices, systems and methods described herein use oscillation vibration patterns to induce increased milk flow from the breast during pumping, through one or more mechanical pathways. In various examples and embodiments, the devices, systems and methods may produce vibrations (or the vibratory waveform) with any suitable pattern, size, shape, timing, etc. For example, in any given embodiment, the frequency of the vibrations or oscillations may range from as low as just above 0 Hz as high as 10 MHz. There may be an ideal frequency range of the vibrations for comfort and the ability of the woman to feel the vibrations, which may for example be in a range of about 5 Hz to about 10 Hz. Alternatively, a wider range of about 2 Hz to about 20 Hz may be ideal in some embodiments. Generally, if the vibration frequency is too high, the woman will not feel the vibrations. On the other hand, high frequency vibration in the ultrasound range might be helpful in some instances, such as for unclogging milk ducts and alleviation of mastitis.

Just as any suitable type of vibrations may be applied, according to various embodiments, any suitable devices may be used to produce the vibrations, examples of which are described below. Therefore, this application should not be interpreted as being limited to any particular type or pattern of vibrations or any particular device for inducing vibrations.

As just mentioned, this application describes devices, systems and methods that help enhance breast milk pumping by vibrating the milk ducts to increase the volumetric flow rate of the milk. A typical breast pump includes a vacuum motor and a solenoid. During each pumping cycle, the vacuum motor turns on, creating pressure at the breast and thus helping express milk. At the end of the cycle, the pressure is released by turning on the solenoid to normalize the pressure in the breast pump flange. The cycle is then repeated. By "repeated," it is meant simply that multiple cycles run in succession, for as long as the breast pump is activated. In some cases, the same cycle may be repeated over and over again—i.e., cycles with the same waveform. In other embodiments, the cycles may differ. For example, two different cycles may alternate. Or the cycle waveform may change over time. Or the cycle waveform may be adjustable or have automatic changes over time, according to a built-in algorithm. Therefore, in any given embodiment, the cycles may repeat or vary over time.

In one embodiment of breast pumps according to the present disclosure, to generate the vibratory waveform, the breast pump uses pulse width modulation on the control signal to the vacuum motor to turn the motor on and off rapidly. The vacuum motor can be driven by an h-bridge to cyclically create a vacuum and release the vacuum, by alternating the polarity to the motor. In some embodiments, the breast pump may include more than one vacuum pump. One vacuum pump provides the non-vibratory waveform, while the other vacuum pump provides the vibratory effect by increasing and/or decreasing pressure.

In another embodiment, a method for inducing a vibratory waveform in a breast pump cycle may involve modulating the solenoid while the vacuum is on. The breast pump may include more than one solenoid. One solenoid, selected to provide a fast release time, may be used to release the vacuum. The other solenoid, selected to have a slow release time, may be used to provide the vibratory waveform.

In other embodiments, the vibratory waveform may be generated mechanically by the design of the vacuum pump. For example, in a multiple n-piston-based vacuum pump, m pistons (where m<n) can be non-connected or connected to a release valve, which will create the stepwise vibratory pressure profile. In the multiple n-piston-based vacuum pump, the pistons may be aligned asymmetrically, to provide the vibratory waveform. Alternatively or additionally, valves within the piston vacuum pump may be purposely designed to be "leaky," to provide a partial release in vacuum to create a more pronounced vibration effect. Other mechanical alterations may include designing a release valve that automatically turns on and off rapidly to create the vibration. The vibration may also be created by a motor squeezing and releasing a bulb or balloon that is in-line with the vacuum pump.

In various embodiments, vibrations may be generated on the flange or bottle assembly of the breast pump device. Mechanisms that may be incorporated into a breast pump device to generate vibrations on the flange or bottle assembly include, but are not limited to, a linear or rotary vibration motor, a piezo-electric crystal, a shape memory alloy, a speaker, and a magnet. For example, one breast pump device may include a motor positioned directly on the flange. The motor may include an offset weight attached to the motor shaft, to create vibrations in the flange, which are transmitted to the breast and ultimately to the milk ducts.

Alternatively, vibrations may be generated using an external device. Such a device may be placed or worn on the breast and may create vibrations by any suitable mechanism(s).

The frequency and amplitude of the generated vibrations may be varied, in order to induce or sustain letdown, make letdown happen easier by lowering the sensation threshold of the body, and/or vibrate the milk to make it flow more easily by reducing the shear stress of the fluid and/or frictional coefficients of the fluid against the ducts. To conserve battery power, generated vibrations may have a low frequency and a low amplitude. Alternatively, any combination of frequency and amplitude may be used.

Any features or components described in this application for generating a vibratory waveform in a breast pump may be used with or incorporated into any suitable powered or non-powered breast pump device. The vibratory waveform may be used as a third method for controlling the pumping apparatus, in addition to (or as an alternative to) adjusting the breast pump's cycle speed and/or suction level. In various embodiments, the vibratory waveform may be tuned by the user and/or by a feedback control mechanism built into the device. The vibratory waveform may help vary the vibration level within the waveform or against the breast tissue so that the variables of suction, vacuum and vibration could be independently controlled by the user manually or by an automated or adaptive learning computer algorithm, to support the optimization of milk output.

Referring now to FIGS. 2-10B, according to various examples and embodiments, many different vibratory waveform shapes, types, patterns, sizes, etc. may be generated and used in a breast pump device to enhance milk extraction from a breast. FIGS. 2-10B illustrate examples of such vibratory waveforms. Later figures depict examples of devices that may be used to generate the vibratory waveforms. In general, any vibration inducing device described herein may be used to generate vibrations having any waveform or other characteristics, unless specifically described otherwise. Thus, the scope of the present application should not be limited to the use of any specific vibration device or any specific vibratory waveform.

Figure 2:
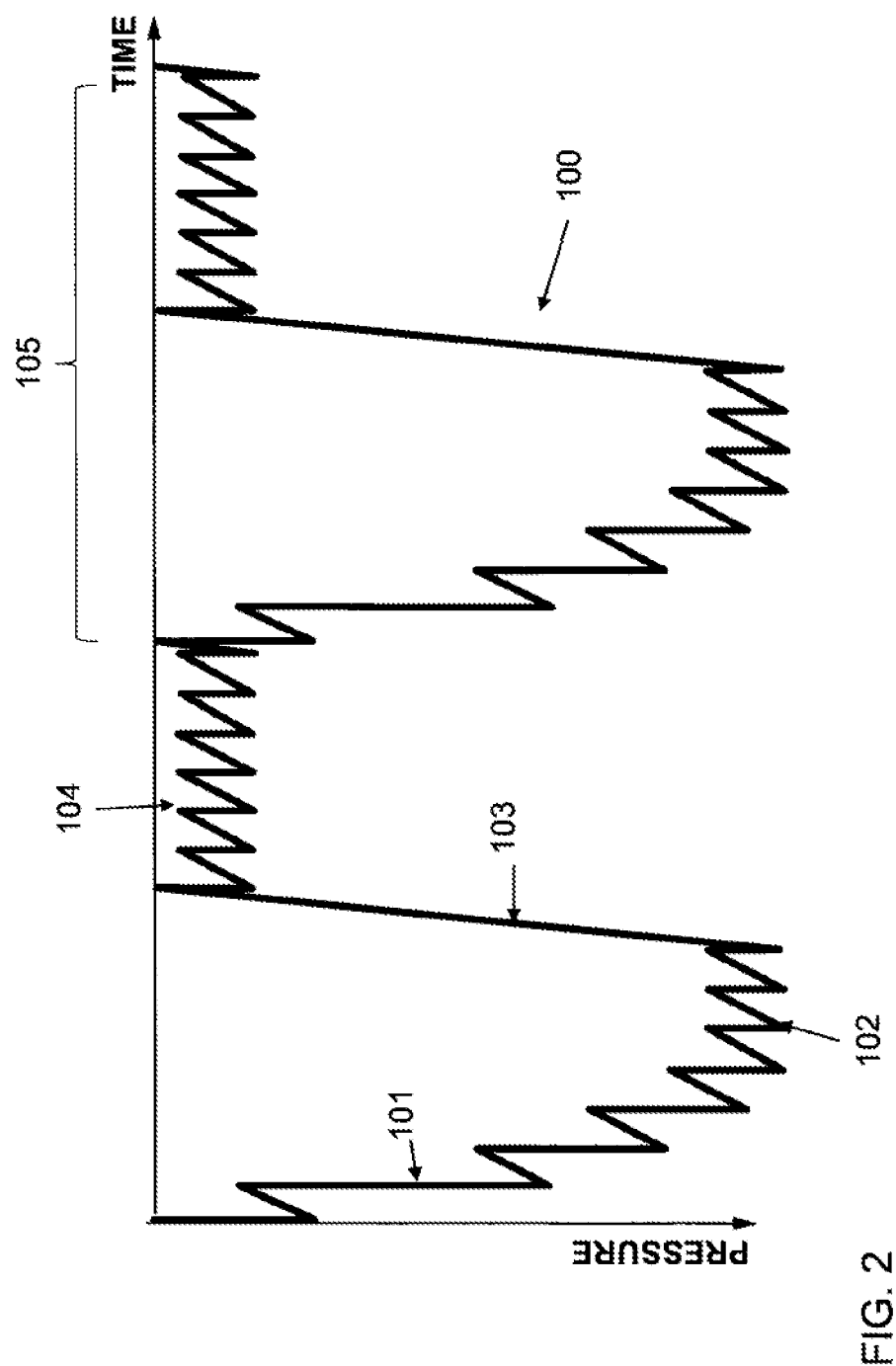
FIG. 2 is a time versus pressure diagram, showing a vibration applied via a breast pump by modulating a suction waveform along part of the suction induction breast pump curve, according to one embodiment.

FIG. 2 is a time versus pressure graph that shows one embodiment of a vibratory waveform 100, which may be generated in a breast pump using the methods and devices described herein. Each complete cycle 105 of the vibratory waveform 100 includes an increasing vacuum segment 101 (or "reduction in pressure segment"), a vacuum hold segment 102, a vacuum release segment 103 (or "normalizing the pressure segment" or "venting segment"), and a final hold segment 104 (or "normalized pressure hold segment"). In this embodiment, the vibrations of the vibratory waveform 100 are applied during the vacuum segment 101, the vacuum hold segment 102, and the final hold segment 104, but not during the vacuum release segment 103. The oscillatory effect of the normalized pressure hold segment 104 may occur at the normalized pressure, slightly higher than normalized pressure, or most preferably lower than normalized pressure—e.g., a slight vacuum, to help maintain the breast in the correct suction position within the flange of the breast pump. The waveform 100 may be repeated for any number of cycles 105, in the same pattern or a different pattern. The pattern of the waveform 100 may be changed, according to various embodiments, automatically, manually or both. For example, the pattern may be adjusted manually by the user by varying settings of the breast pump device. Alternatively or additionally, the pattern may be adjusted automatically by a control unit of the breast pump device, which may be directed via computer software through tunable or reactive learning interactions.

As mentioned above, currently available breast pump systems typically allow a user to adjust (or adjust automatically) the cycle speed and suction pressure of the system. Referring to the waveform 100 of FIG. 2, adjusting the cycle speed would change the "width" of each cycle 105 along the horizontal "time" axis of the graph. A faster cycle speed equates to higher frequency, and a lower cycle speed to lower frequency. Adjusting the suction pressure would change the "height" or "depth" of the curve along the vertical "pressure" axis of the graph. According to various embodiments described herein, the user and/or the control unit of the breast pump system may adjust vibrations in addition to or as an alternative to adjusting cycle speed and/or suction pressure. Vibration adjustments may include, for example, turning vibrations on or off, making vibrations occur over different portions of the waveform 100, and/or changing a pattern or depth/strength of each vibration. In some embodiments, for example, the breast pump system may include one or more dials, switches, buttons, sliders or the like, for making the adjustments. Some embodiments may include a separate controller, such as a remote control unit or a computer application downloaded on a smart phone, tablet, etc. Generally speaking, any given embodiment may allow a user to adjust or control vibrations, cycle speed and/or suction pressure in any suitable combination.

Figure 3:
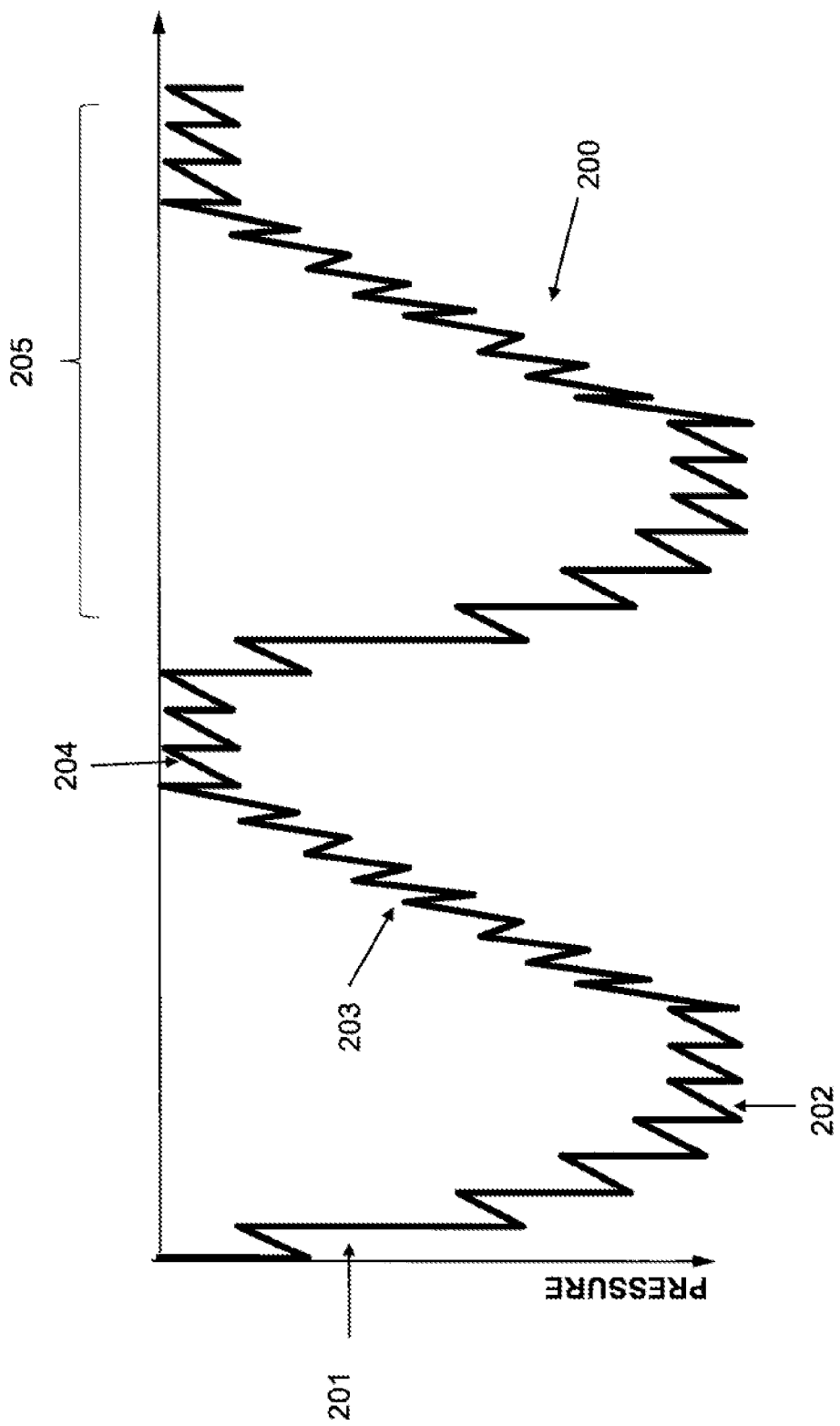
FIG. 3 is a time versus pressure diagram, showing a vibration applied via a breast pump by modulating a suction waveform along all of the suction induction breast pump curve, according to an alternative embodiment.

Referring now to FIG. 3, another embodiment of a vibratory waveform 200 for use with a breast pump device is illustrated. In this embodiment, the waveform 200 includes an increasing vacuum segment 201, a vacuum hold segment 202, a slow vacuum release segment 203, and a restart segment 204 at or near normalized pressure, which may contain a vibratory pattern. In this embodiment, vibrations are applied throughout the entire cycle 205 of the waveform 200, although vibrations during the restart segment 204 are optional. According to various embodiments, the segments 201, 202, 203, 204 may repeat in any configuration of these patterns or other patterns of vibration, suction, stair step, etc. The vibration patterns disclosed herein are also be interchangeable between each other, so that a user of a breast pump device may experience multiple different types of patterns within one operational period of the device.

Figure 4:
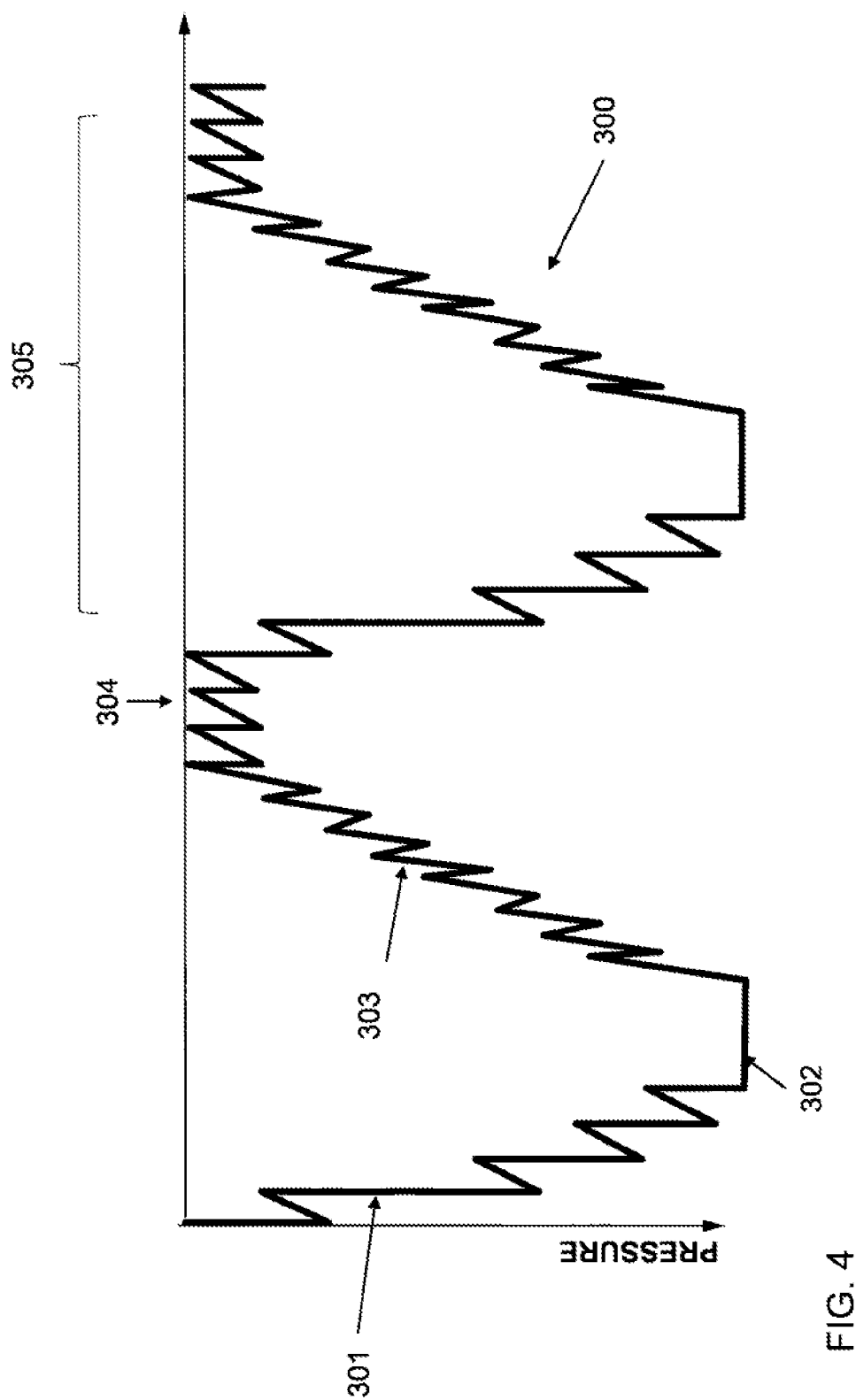
FIG. 4 is a time versus pressure diagram, showing a vibration applied via a breast pump by modulating a suction waveform along the suction induction breast pump curve, except for a resting hold state at the lowest point in the vacuum, with no vibration or oscillation effect, according to one embodiment.

FIG. 4 shows another embodiment of a vibratory waveform 300 for use with a breast pump. In this embodiment, each cycle 305 of the waveform 300 includes an increasing vacuum segment 301, a hold vacuum segment 302, a slow vibratory vacuum release segment 303, and a near normalized pressure segment 304. In this embodiment, vibrations are applied during all segments other than the hold vacuum segment 302, which is vibration free. For this waveform 300, the normalize pressure segment 304 is optional, meaning that in some embodiments one cycle 305 may end with the vibratory vacuum release segment 303, and the next cycle may immediately begin with the increasing vacuum segment 301.

Figure 5:
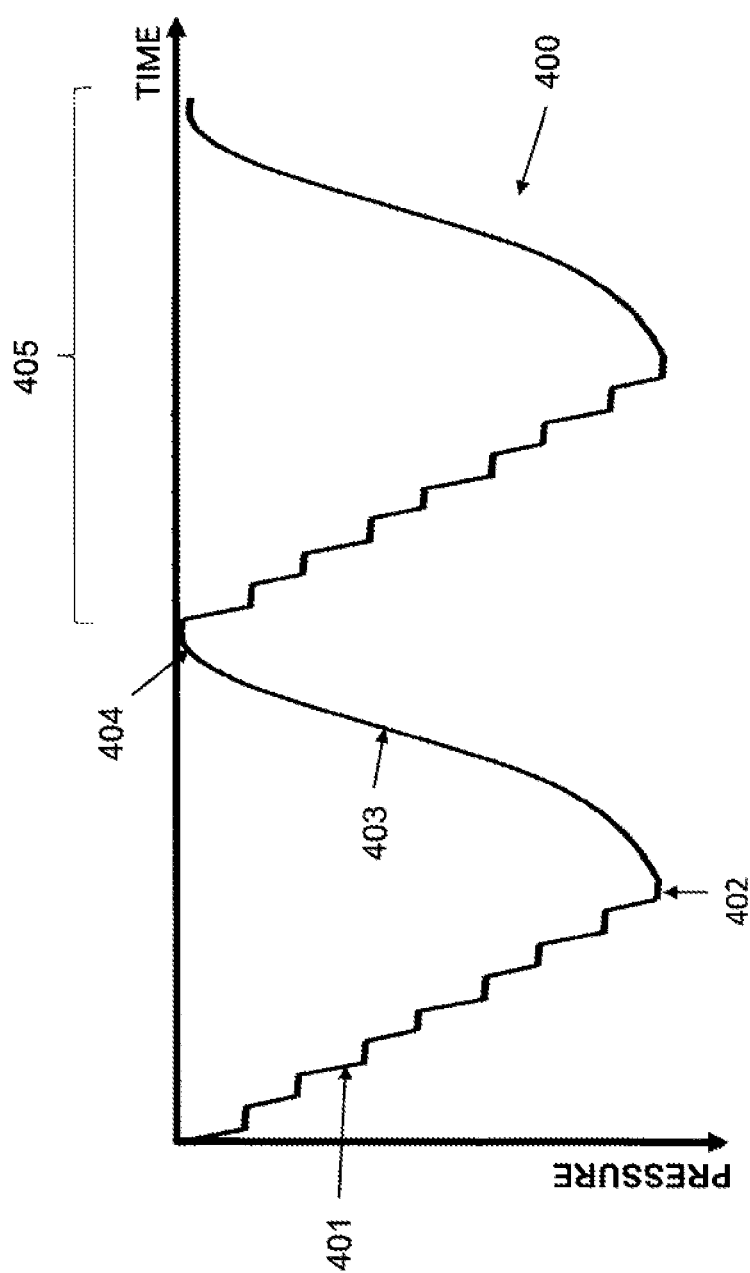
FIG. 5 is a time versus pressure diagram, showing a breast pump suction curve with a stair-step vibratory stimulation pattern of short stair-step bursts, according to one embodiment.

FIG. 5 depicts another embodiment of a vibratory waveform 400 for a breast pump suction profile. In this embodiment, each cycle 405 of the waveform 400 includes a vacuum segment 401, a maximum vacuum segment 402, a vacuum release segment 403, and an end cycle segment 404. The vacuum segment 401 has a stair-step pattern of vibrations applied to it. The maximum vacuum segment 402 may include a hold period, during which vacuum is maintained, but such a period is optional.

Figure 6:
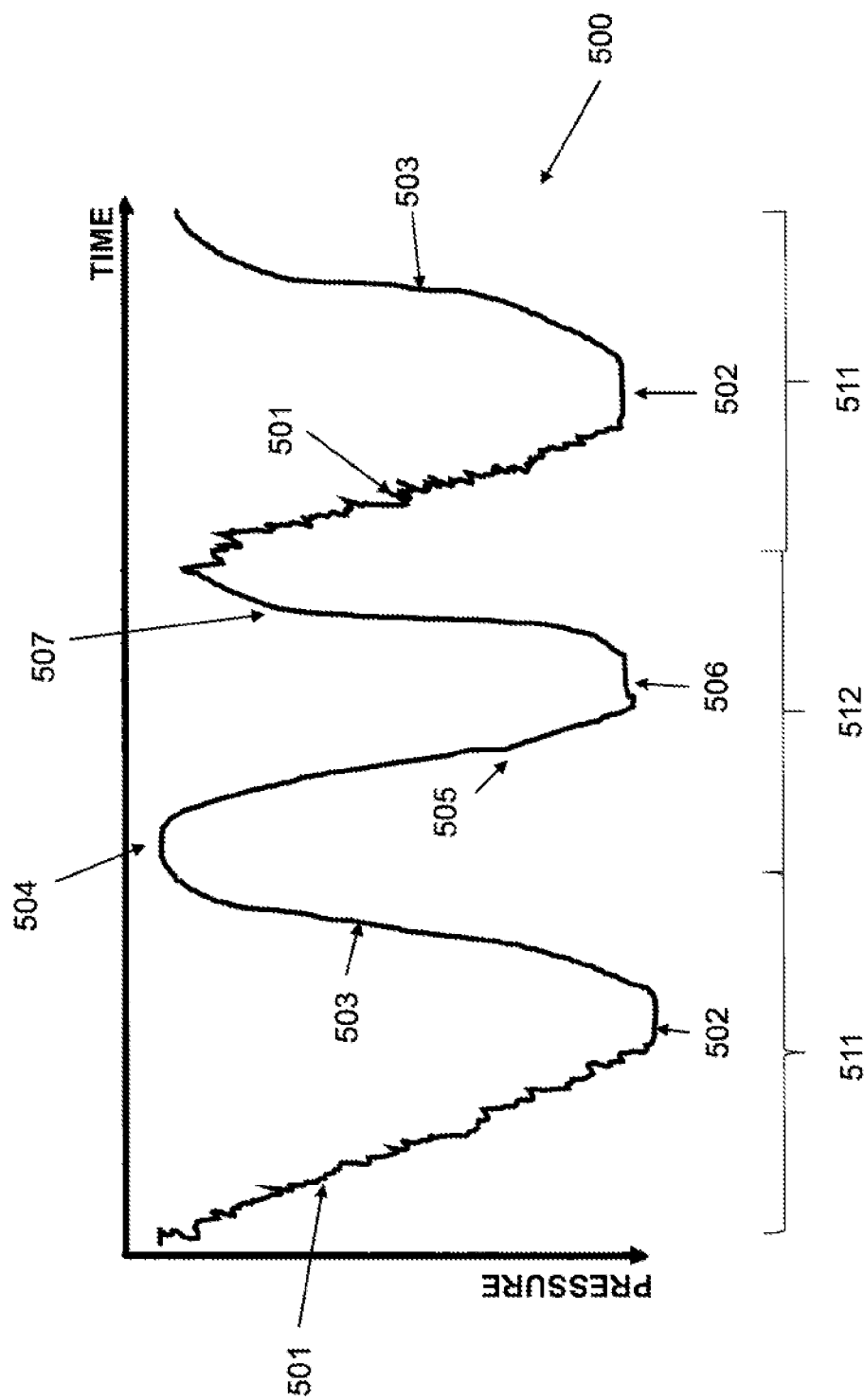
FIG. 6 is a time versus pressure diagram, showing a breast pump suction curve with alternating and/or independently modulated wave cycles, one including an oscillating effect and another including no oscillating effect, according to one embodiment.

With reference now to FIG. 6, another embodiment of a vibratory waveform 500 for a breast pump is illustrated. This embodiment includes two types of waveform cycles—a first cycle type 511 and a second cycle type 512. The first cycle type 511 includes an increasing vacuum segment 501 with micro-oscillation vibrations, and a hold vacuum segment 502, a vacuum release segment 503 and an end segment 504, all with no vibrations. The second cycle type 512 includes an increasing vacuum segment 505, a hold vacuum segment 506, and a vacuum release segment 507, all with no vibrations. These cycles 511, 512 of the vibratory waveform 500 may be performed in any order desired by a user. The embodiment of FIG. 6 includes two different types of cycles 511, 512 in a single waveform 500, but other embodiments may include more than two different types of cycles, different patterns of differing cycles, oscillation between two or more cycle profiles, and/or the like. In various embodiments, any of the waveform shapes, patterns, types and/or sizes described herein may be combined with any other waveform shapes, patterns, types and/or sizes, whether described herein or not, in any combination and number, without departing from the scope of this disclosure.

Figure 7:
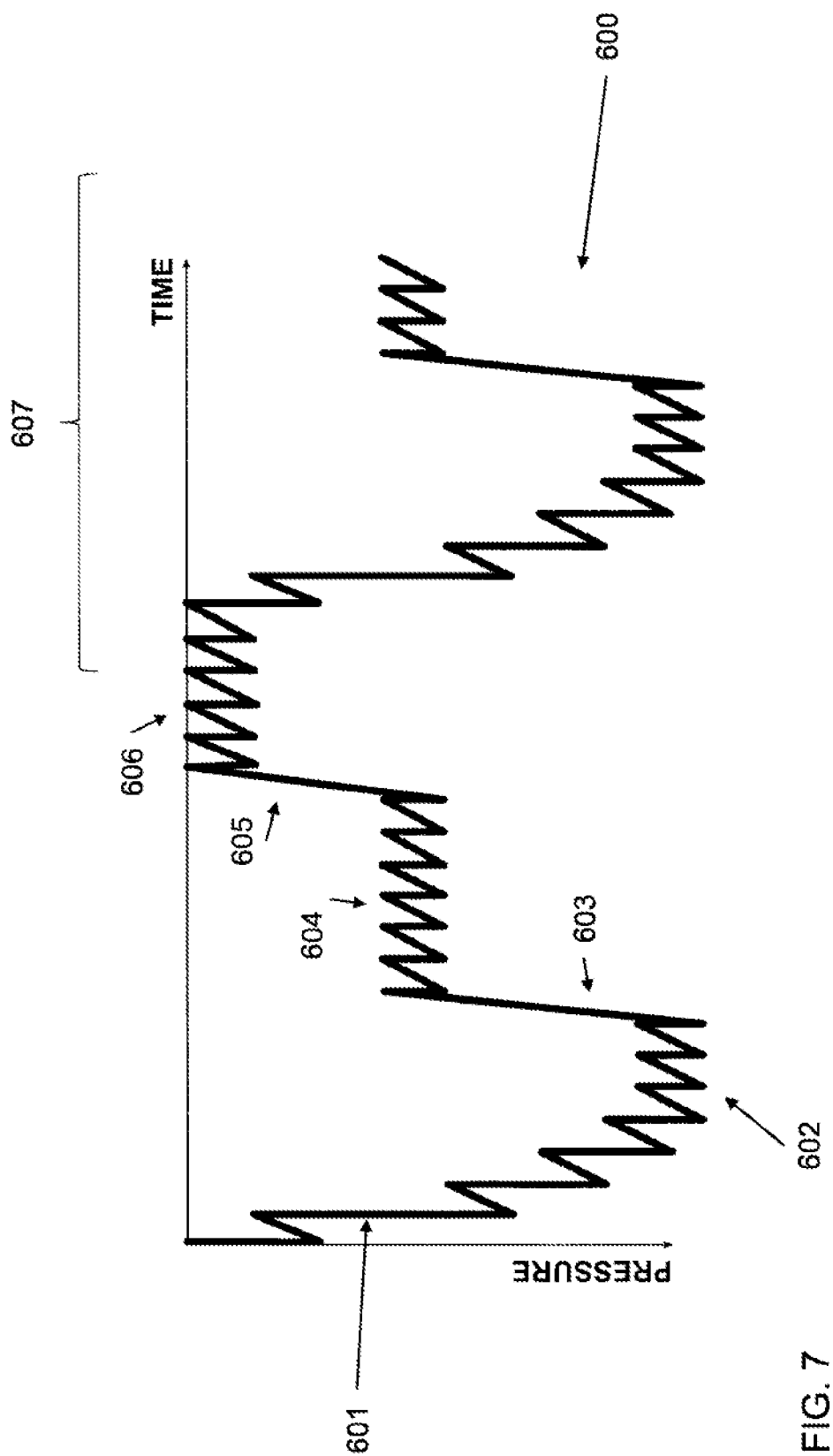
FIG. 7 is a time versus pressure diagram, showing a breast pump suction curve including a drop-in pressure, a stair-step increase in pressure, and an additional cycle, with vibratory effects on at least part of the waveform curve segments, according to one embodiment.

FIG. 7 depicts another embodiment of a vibratory waveform 600 for a breast pump suction curve, in which each cycle 607 includes a vacuum increase segment 601, a vacuum hold segment 602, a first vacuum release or vent segment 603, a partial reduced vacuum hold segment 604, a second vacuum release or vent segment 605, and an end of cycle segment 606, at which pressure is near ambient normal. Vibrations are applied at all segments other than the first vacuum release segment 603 and the second vacuum release segment 605. Variations on this embodiment of the waveform 600 may include different combinations of more or fewer hold segments, vacuum increase segments and/or vacuum decrease segments. Additionally, the same elongated stair-step vibration pattern used in the vacuum increase segment 601 may be applied in one or both of the vacuum release segments 603, 605, in alternative embodiments, to more slowly reduce the vacuum to one or more limits, to facilitate the stimulation of letdown and/or the stimulation or production of breast milk and/or colostrum.

Figure 8B:
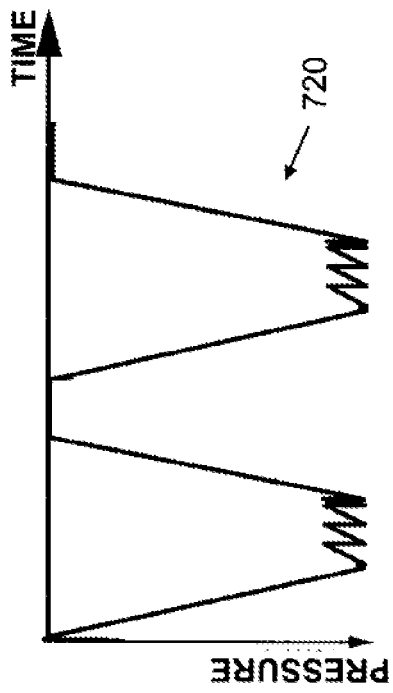
FIGS. 8A-8D are time versus pressure diagrams that depict exemplary vibratory waveforms, each of which includes a vibration segment and a smooth segment during parts of the wave rise, fall, and/or hold segment(s), according to one embodiment.
Figure 8D:
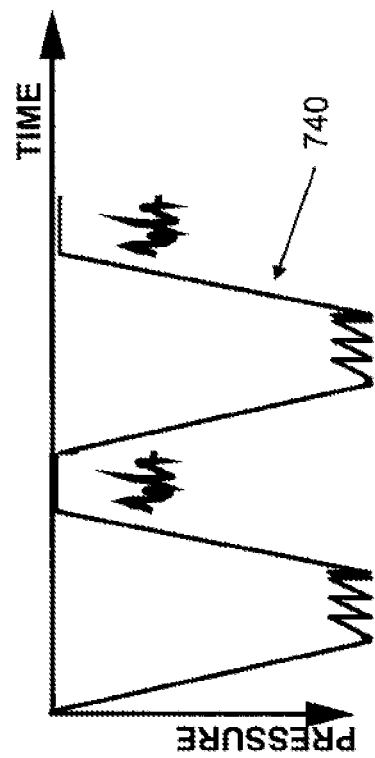
Figure 8A:
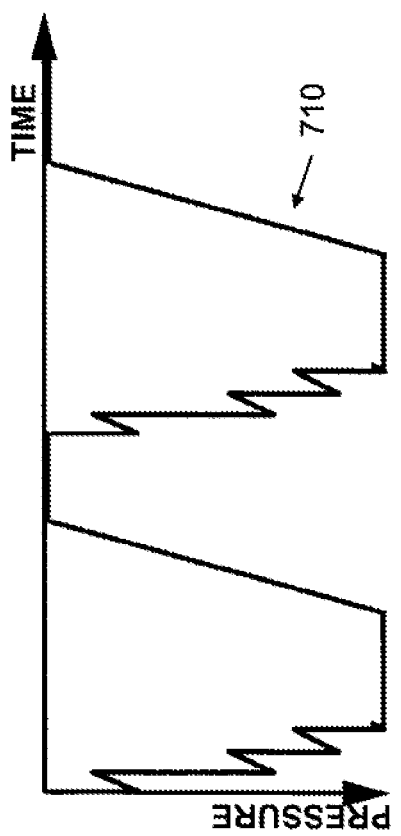
Figure 8C:
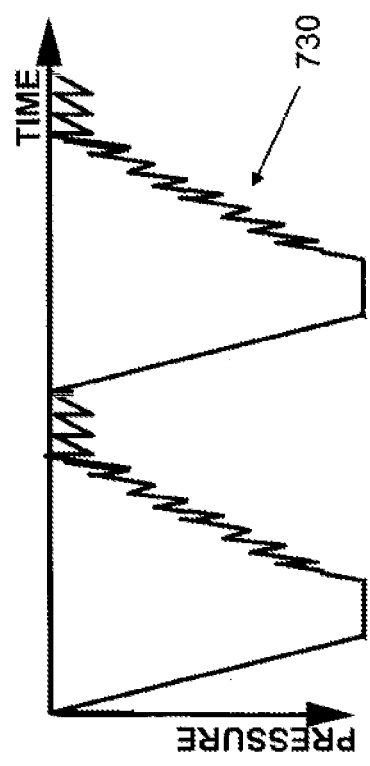

FIGS. 8A-8D show four different embodiments of breast pump suction waveform profiles with varying segments of oscillation and/or vibratory effects. FIG. 8A shows a waveform 710 with a vibration effect on the increase in vacuum side of the cycle. FIG. 8B shows a waveform 720 with a vibration effect within the maximum vacuum segment. FIG. 8C shows a waveform 730 with a vibration effect during and immediately after venting to a near normalized pressure segment. FIG. 8D shows a waveform 740 with a vibration effect upon venting to a near normalized pressure segment including increasing the pressure slightly above the current atmospheric pressure in which the pump is operating if desired. These effects may be controlled by a micro-processor within the control unit of the breast pump device (or separate from the breast pump device), which can tune the effects of one or more motors and/or one or more solenoids to adjust the effect over different segments of the breast pump to produce the desired effect while pumping the breast.

Figure 9:
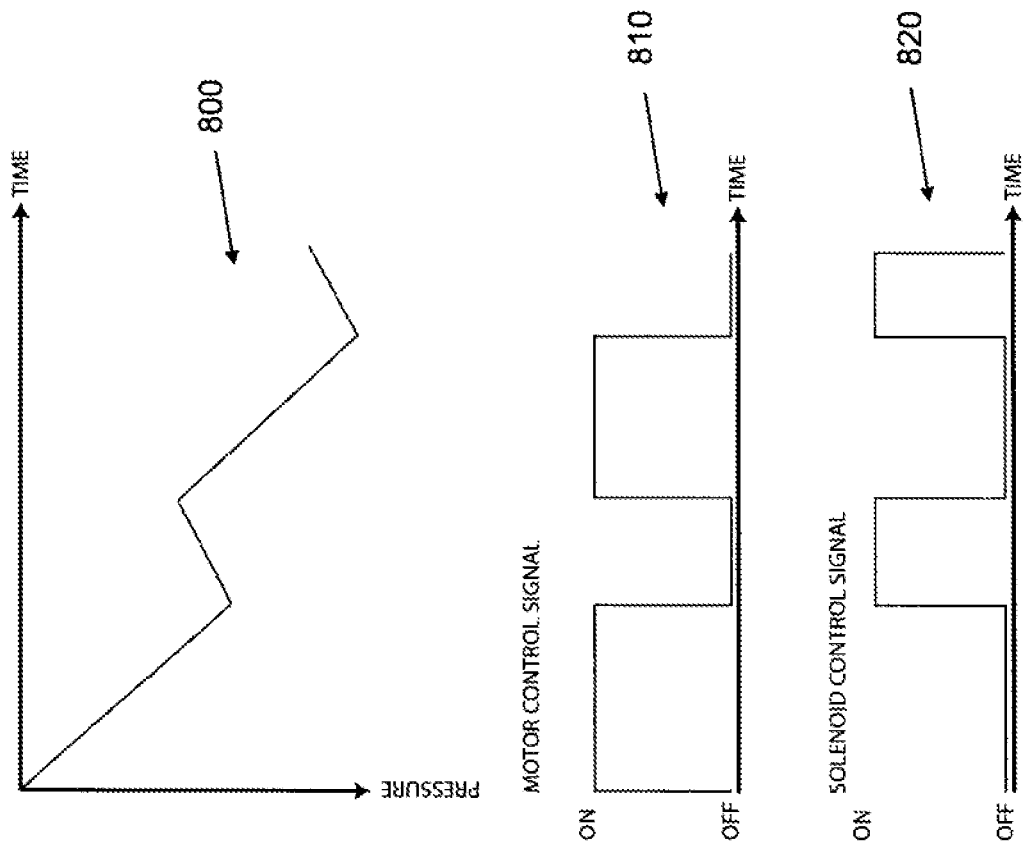
FIG. 9 depicts a time versus pressure curve and exemplary motor and solenoid control signal curves, illustrating a modulating effect of the control signals on an oscillating pressure reduction curve from a breast pump suction waveform, according to one embodiment.

FIG. 9 includes a time versus pressure curve 800 in parallel with a motor control signal on/off curve 810 and a solenoid control signal on/off curve 820. In various embodiments, the motor and/or the solenoid of a breast pump may be tuned/adjusted by a user to produce the desired vibration and vacuum waveform 800 for pumping. This effect and/or the action of the motor(s) and/or solenoid(s) to create the vibrations and/or controlled waveform effect may additionally or alternatively be adjusted by a control unit of the breast pump, programmed with software, to facilitate specific wave forms at different times, as desired by the user and/or as informed to the control unit by sensors or feedback from the user.

Figure 10A:
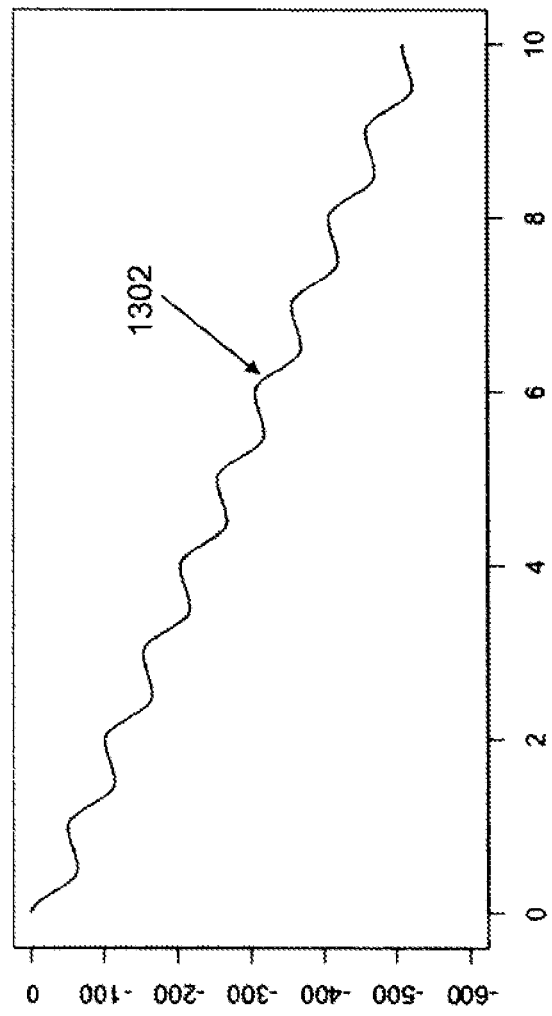
FIG. 10A is a graph showing a vacuum waveform with a stair-step vibration pattern, according to one embodiment.
Figure 10B:
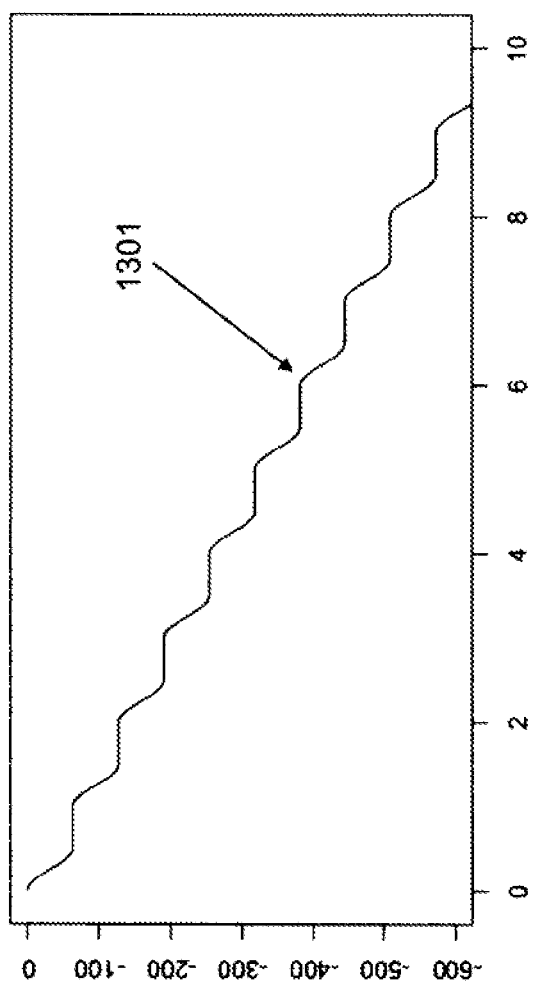
FIG. 10B is a graph showing a vacuum waveform with an oscillating increase and decrease vibration pattern, according to an alternative embodiment.

FIGS. 10A and 10B are graphs illustrating two different embodiments of vibratory waveforms. In FIG. 10A, the vibratory waveform 1301 has a stair-step pattern. One method for generating such a pattern is to rapidly turn the breast pump on and off repeatedly. This may be achieved, for example, by using a stepper motor or a DC motor. When the breast pump is on, vacuum is increased. When the pump is off, vacuum is held.

In FIG. 10B, the vibratory waveform 1302 has a wavy pattern created by repeated oscillatory increases and decreases in vacuum. One method for generating this type of wavy patterned waveform is by having a separate vacuum motor or m piston (where m≥1 and m≤n) within a n-piston vacuum motor increase and/or decrease the vacuum within the system. Another method to generate this pattern is a controlled partial release of vacuum by using a solenoid.

Figure 11:
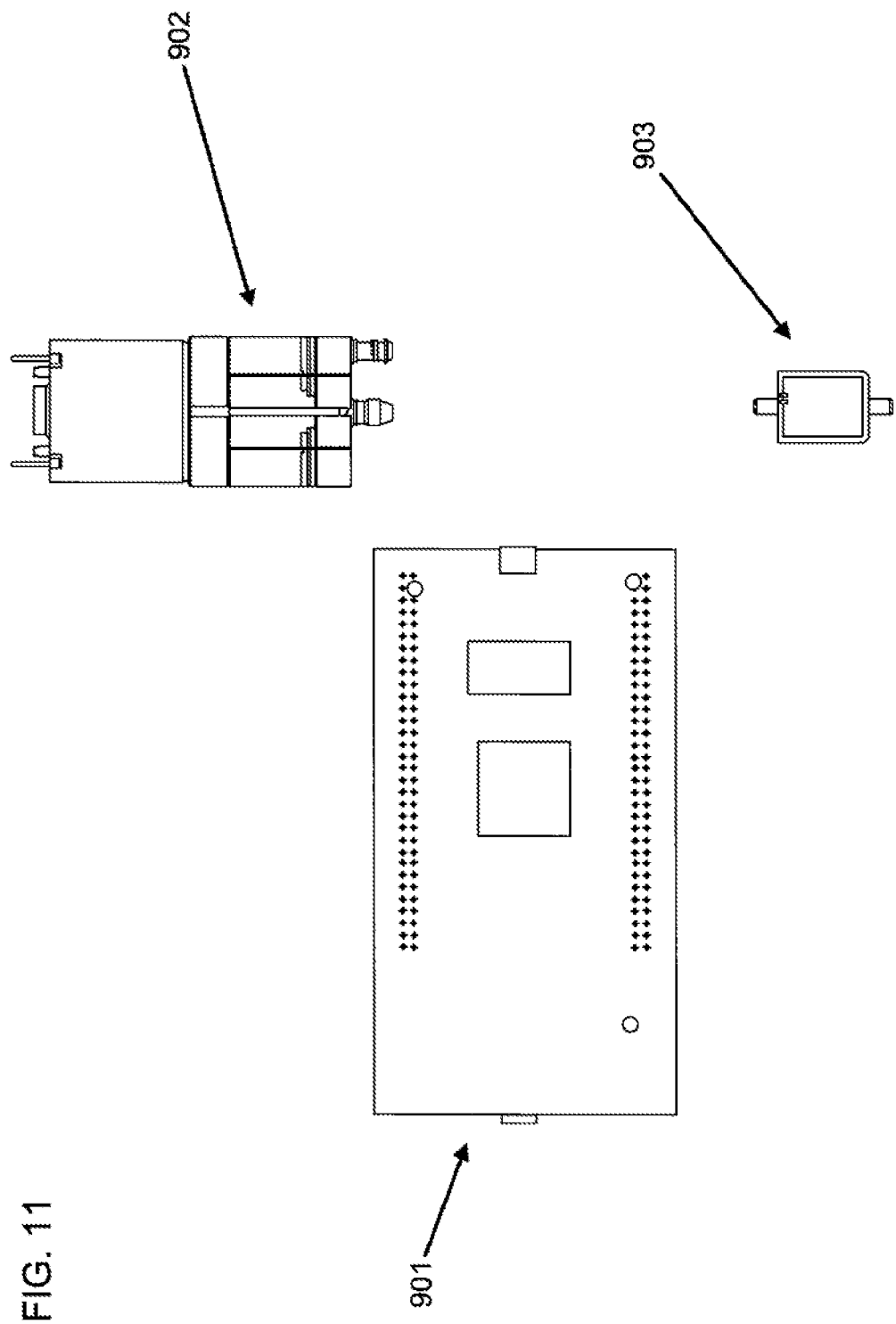
FIG. 11 illustrates a PCB, a pump motor, and a solenoid of a breast pump device, of which one or more may be used to drive activity of the breast pump waveform and waveform effects, according to various embodiments.

FIG. 11 illustrates three components that may be included in a breast pump device or system and that may be used, in various combinations, to provide a vibratory waveform. These components may include a printed circuit board (PCB) 901 (or other similar electronic components), a motor 902, and a solenoid 903. Various embodiments of a breast pump may include multiple PCBs 901, multiple motors 902, and/or multiple solenoids 903, and that fact will not be repeated each time any of these components is mentioned. The PCB 901 may work together with the motor 902 and/or the solenoid 903 to provide vibrations to the breast pump cycle, as described above. In alternative embodiments, other types of pressure venting devices may be passively, electrically, or mechanically actuated in combination with the pump motors, pressure regulator valves, and/or other components, to create the desired wave form within the suction induction curve.

Figure 12:
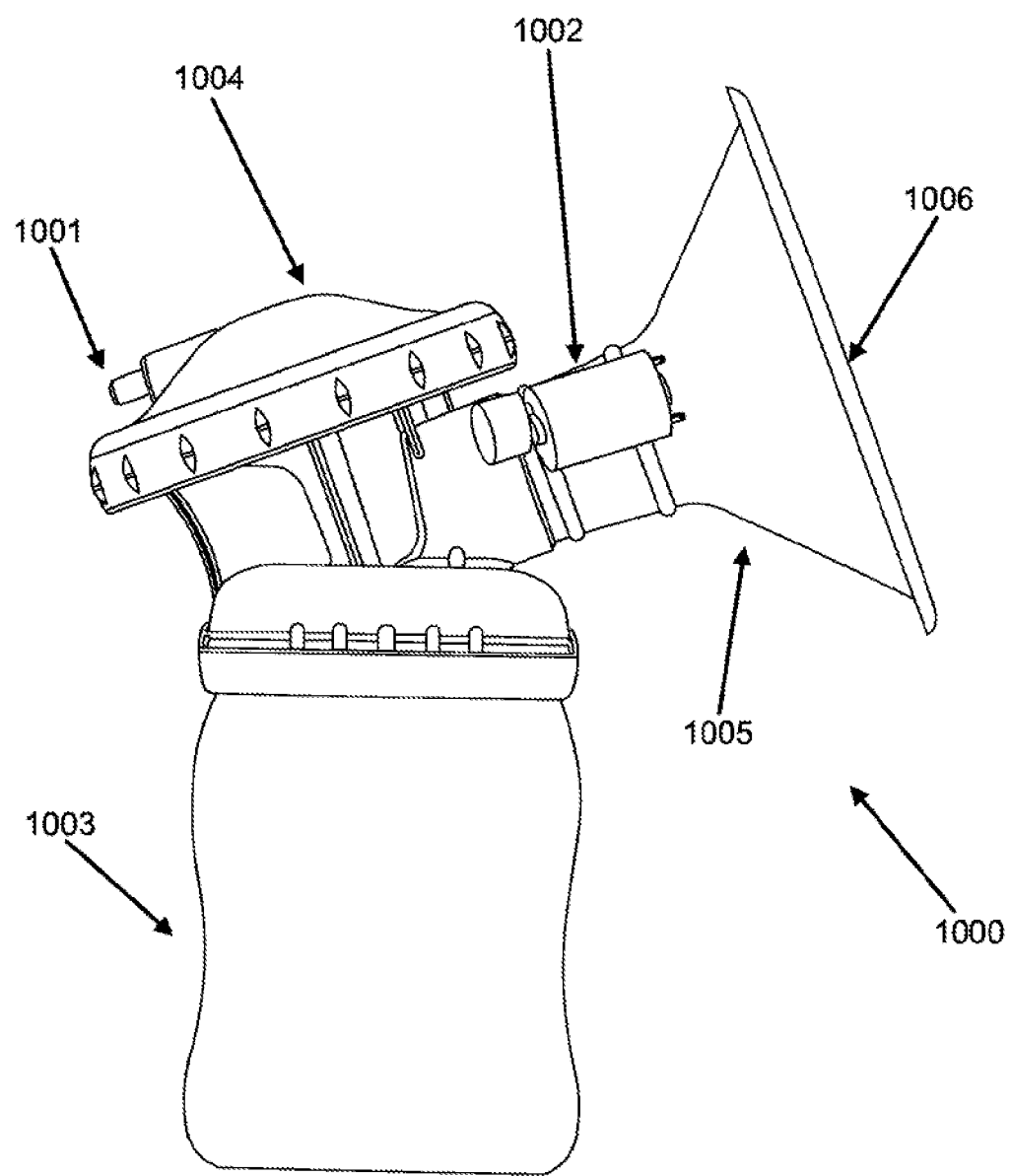
FIG. 12 is a side view of a breast pump flange and receptacle, with a vibration motor coupled with the breast pump flange, according to one embodiment.

FIG. 12 is a side view of a breast pump device 1000, according to one embodiment. This and several following figures will refer to the breast contacting portion of the breast pump system as the "breast pump device." Not shown are the control unit (or "pump") and the tubing for connecting the breast pump device with the control unit. As mentioned previously, the specific terminology used for various components of a breast pump system should not be interpreted as limiting.

In this embodiment, the breast pump device 1000 includes a vacuum port 1001, a pressure regulation diaphragm 1004, a collection receptacle 1003 for milk or colostrum, a vibration device 1002, and a funnel 1005 with an opening 1006 for accepting a breast. The vibration device 1002 is a small vibration inducing motor attached to a proximal portion of the funnel 1005. In alternative embodiments, the vibration device 1002 may be attached to a different part of the breast pump device 1000, such as but not limited to a flange, the collection receptacle 1003 or the diaphragm 1004. In the pictured embodiment, the vibration device 1002 directly vibrates the funnel 1005, which conducts the vibrations into the breast tissue received in the opening 1006. The vibration device 1002 may generate any of the various types and patterns of vibratory waveforms described above or any other suitable vibrations.

Figure 13:
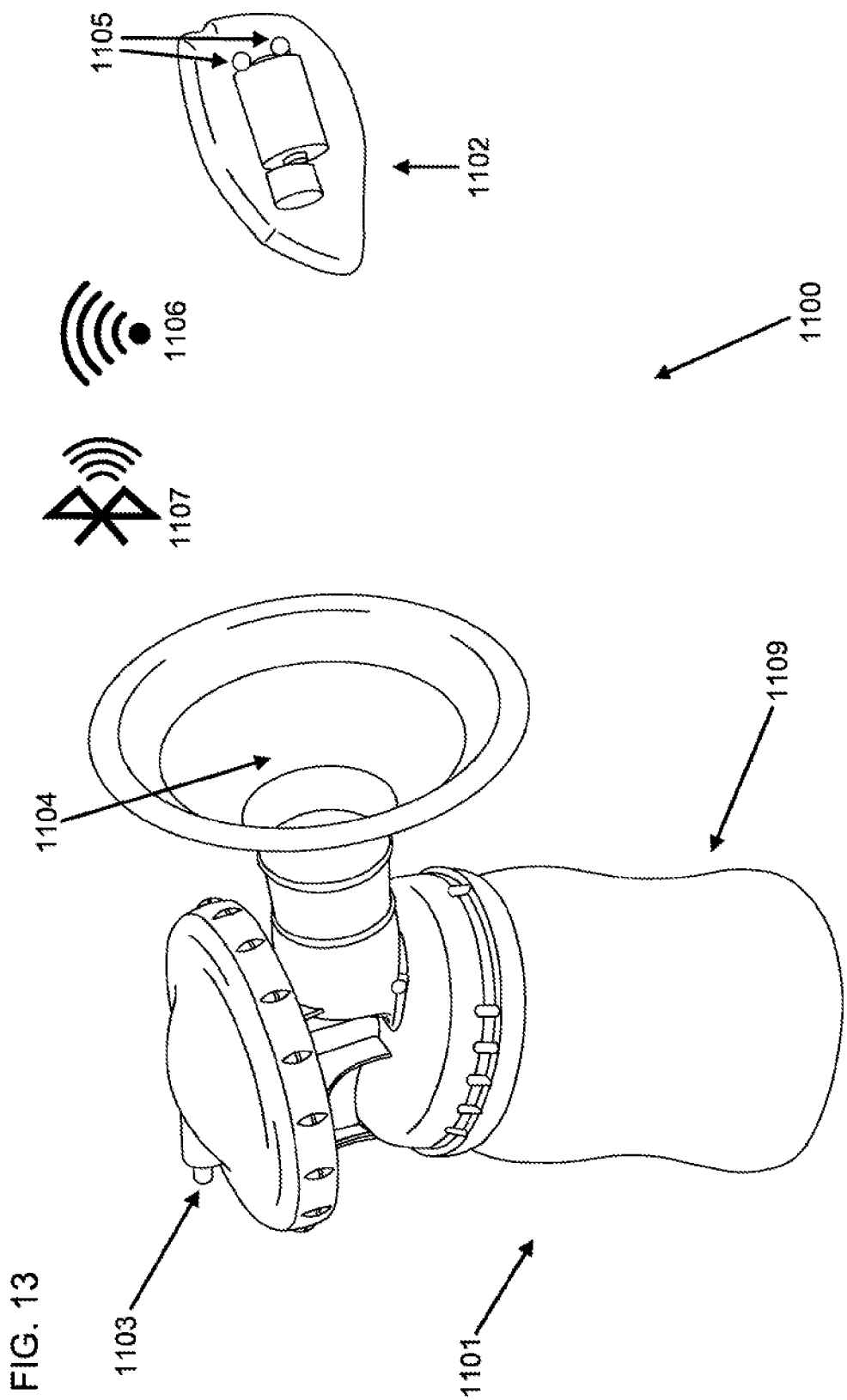
FIG. 13 is a perspective view of a breast pump system including a breast pump flange and a separate vibration motor designed to be held by the user to mechanically vibrate the breast, according to one embodiment.

Referring now to FIG. 13, in another embodiment, a breast pump system 1100 may include a breast pump device 1101 and a separate vibration device 1102. Again, the source of suction—i.e., the breast pump housing mechanism with the motor(s), power cord, etc.—is not shown, but it may be included as part of the system 1100. The breast pump device 1101 includes a vacuum port 1103, a funnel 1104 and a collection receptacle 1109, among other parts. The separate vibration device 1102 may include a small motor for creating vibrations, and it may be held by the user against the breast or attached (e.g., adhesive) temporarily to the breast. The vibration device 1102 may include one or more signal transmitters 1105, receivers and/or transceivers, which communicate with a breast pump control unit (not shown) through wired or wireless connections, such as WIFI 1106 and/or Bluetooth 1107. Although not required, this communication could, in combination with sensors in the vibration device 1102 and/or the breast pump device 1101, provide feedback for the microcontroller to adjust the actuation of the pressure in the breast pump waveform and/or the level of vibration produced by the vibration device 1102. This feedback loop may be preset into the breast pump system 1100 in some embodiments.

Figure 14:
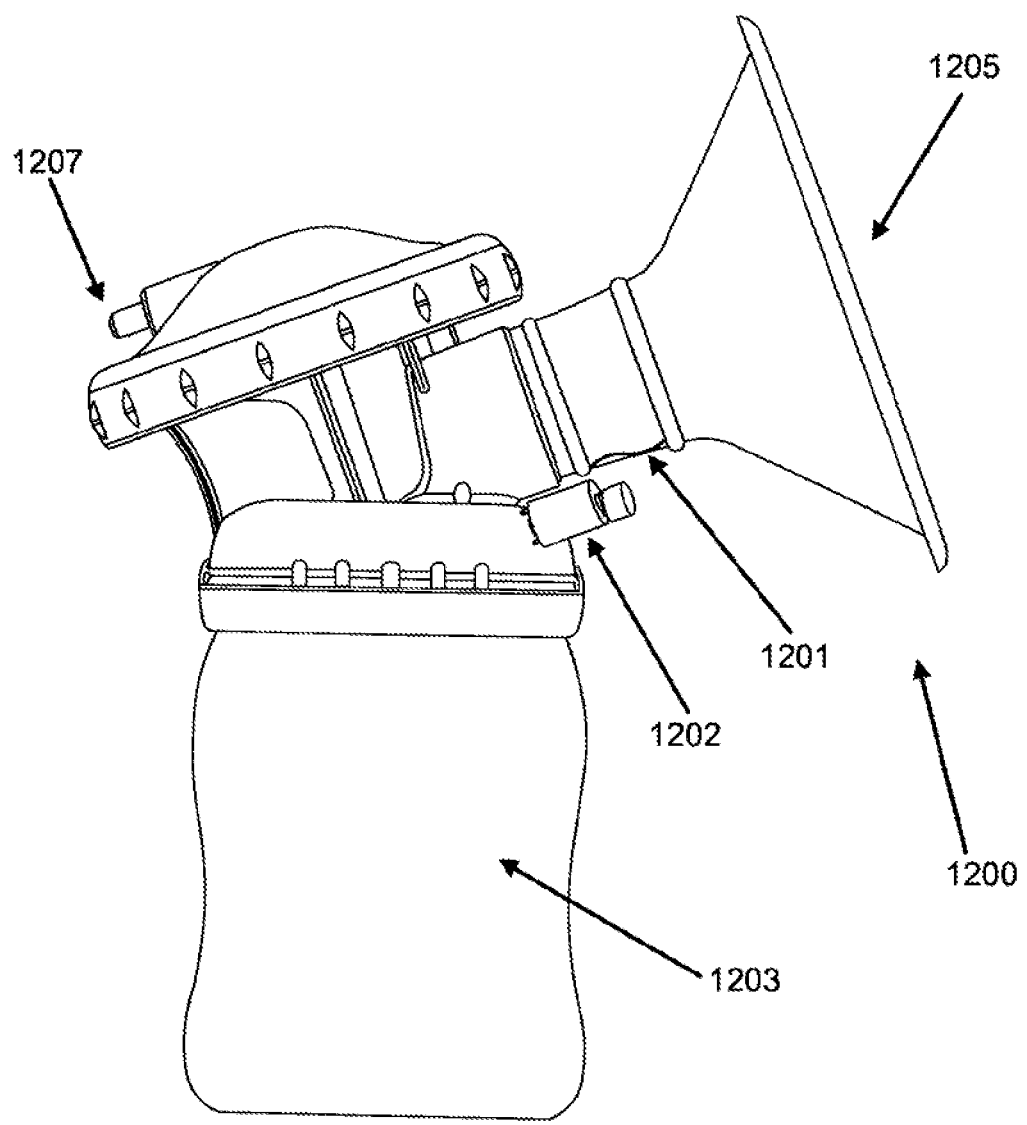
FIG. 14 is a side view of a breast pump flange with a moving membrane and an eccentric motor, according to one embodiment.

FIG. 14 is a side view of a breast pump device 1200 according to another embodiment. In this embodiment, the device 1200 includes all the features of a typical breast pump device, such as a collection receptacle 1203, a funnel 1205, a suction port 1207, etc. In addition, the device 1200 includes an eccentric motor 1202 attached to the top or lid portion of the collection receptacle 1203. The eccentric motor 1202 generates vibrations, which vibrate a membrane 1201 disposed in the funnel 1205, thus resulting in an oscillatory increase and decrease of vacuum (vibration) in the vacuum waveform. The eccentric motor 1202 may communicate to the breast pump control unit through wireless or wired technologies. The eccentric motor 1202 may be attached as part of the breast pump device 1200 or may be a separate piece that can be attached by the user, according to various embodiments.

Referring now to FIG. 15A, one embodiment of a vacuum motor device 1400 for a breast pump system is illustrated. In this embodiment, the vacuum motor device 1400 includes a DC motor 1401 connected to a shaft that moves a piston 1410 connected to a diaphragm 1402. On its down cycle, the piston 1410 pulls the diaphragm 1402 down and thus pulls air from the flange connected to the breast through a first one-way valve 1403, creating a vacuum on the breast. On its up cycle, the piston 1410 pushes the air through a second one-way valve 1404 to the outside world, thus completing the breast pump cycle. In an n=1 n-piston breast pump system, as illustrated by the device 1400 of FIG. 15A, this will produce a stair-step vibratory waveform 1301, such as the one illustrated in FIG. 10A.

Referring now to FIGS. 15B and 15C, to create an oscillatory waveform such as the waveform 1302 in FIG. 10B, some vacuum force must be released from the vacuum motor device 1400. One way to accomplish this is to pass air in the opposite direction through the first one-way valve 1403. In one embodiment, the first one-way valve 1403 may include a diaphragm 1405, as illustrated in top view in FIG. 15B. The diaphragm 1405 includes multiple holes 1406 or apertures, which allow air to pass through. (Any suitable number of holes 1406 may be included.) As illustrated in FIG. 15C, the flap 1407 of the first one-way valve 1403 may include a cut-out portion or other form of opening, to expose part of the diaphragm 1405 and one or more of the holes 1406, which will allow air to pass in the opposite direction through the valve 1403. Air flowing through the first one-way valve 1403 in the opposite direction will cause the oscillatory waveform, because during the up cycle of the piston 1410, some of air is returned to the flange, resulting in a slight decrease in vacuum. This modification of the first one-way valve 1403 can be extended to n>1 in a n-piston vacuum motor.

Figures 16A, 16B, 17:
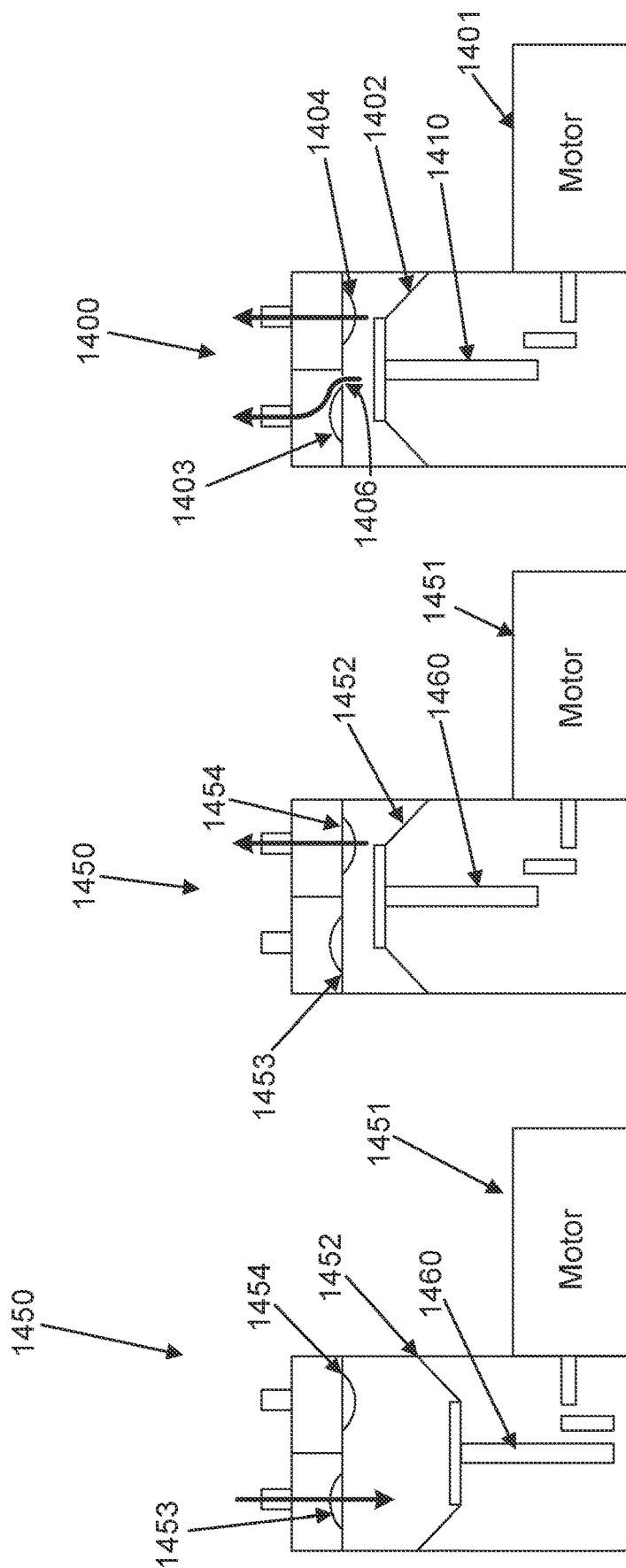
FIGS. 16A and 16B are side views showing operation of a conventional vacuum motor of a breast pump system.
FIG. 17 is a side of the vacuum motor of FIG. 15A, illustrating operation of the motor to generate vibrations in the system, according to one embodiment.

With reference now to FIGS. 16A and 16B, operation of a prior art vacuum motor device 1450 of a breast pump system is illustrated. As illustrated in FIG. 16A, the motor 1451 of the device 1450 drives a piston 1460 to pull down on a diaphragm 1452, which pulls air (down arrow) into the device 1450 through a first one-way valve 1453. This movement of air creates a vacuum force in the breast contacting portion of the breast pump system. In 16B, the motor 1451 then drives the piston 1460 upwards, pushing the diaphragm 1452 up and pushing air (up arrow) out of the device 1450 through a second one-way valve 1454. This pushed-out air releases the vacuum force from the breast contacting portion of the system.

FIG. 17 illustrates operation of the same vacuum motor device 1400 of FIGS. 15A-15C, in contrast to the prior art device 1450. In the FIG. 17 device 1400, air is first drawn in through the first one-way valve 1403, as shown in the prior art device 1450 in FIG. 16A. Then, when the motor 1401 drives the piston 1410 up to push the diaphragm 1402 up, air is pushed out of the device 1400 through the second one-way valve 1404 (straight upward arrow), but unlike in prior art devices, air is also pushed out through the hole 1406 (or multiple holes) in the diaphragm of the first one-way valve 1403 (curved upward arrow). The air escaping through the hole(s) 1406 causes the vibrations in the system. In alternative embodiments, one or more holes may be placed in a part of a breast pump other than the diaphragm, such as in part of the plastic assembly.

Figure 18:
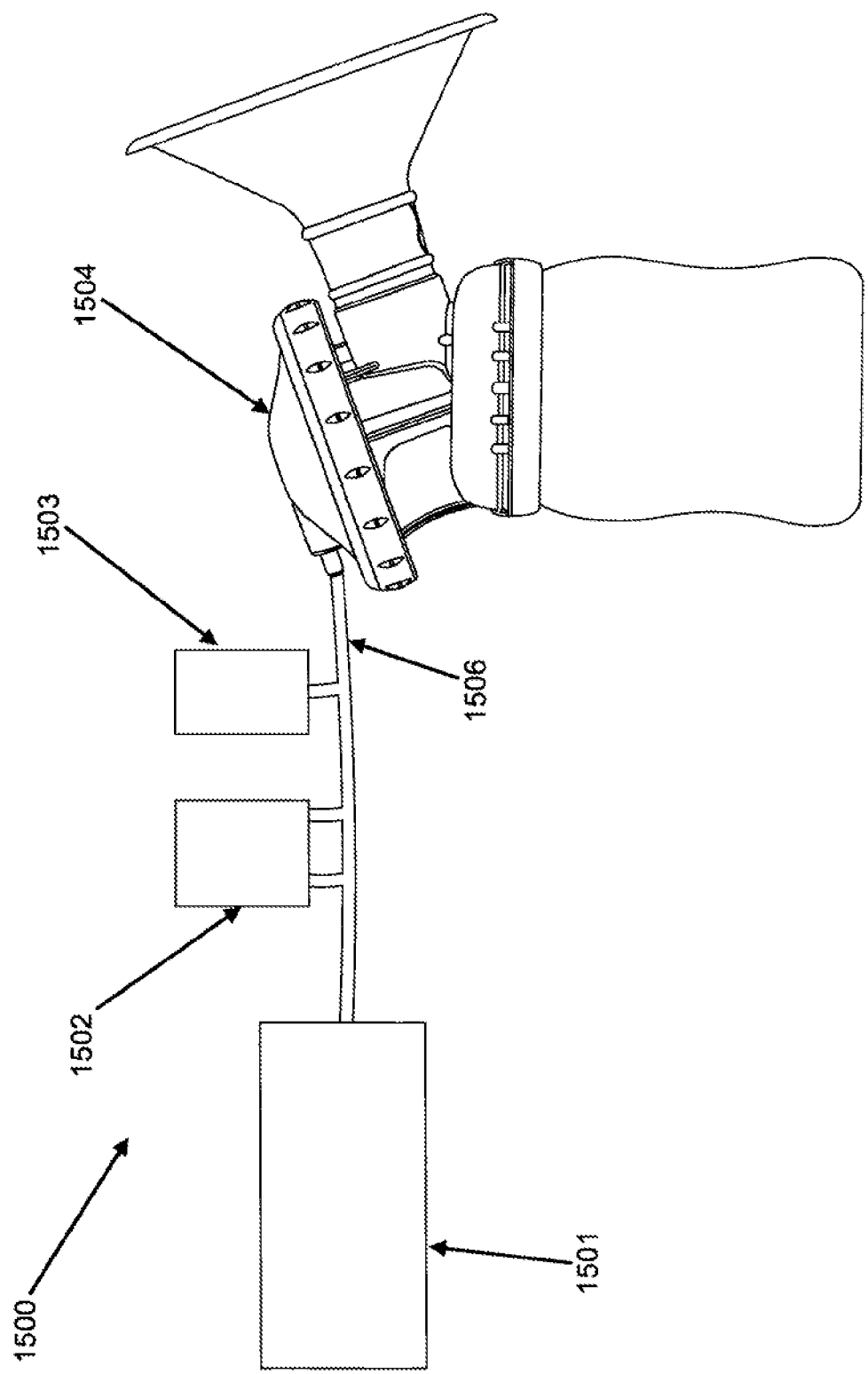
FIG. 18 is a diagrammatic view of a breast pump system that includes a separate motor to generate a vibratory waveform, according to one embodiment.

With reference now to FIG. 18, in an alternative embodiment, a breast pump system 1500 may include a first vacuum motor 1501, a second vacuum motor 1502, a solenoid 1503 and a flange assembly 1504, all connected by a tube 1506 or other suitable connector. The first vacuum motor 1501 provides the main source of vacuum for driving the breast pump system 1500 and providing suction to the flange assembly 1504. The second vacuum motor 1502 generates the vibrations for the vibratory waveform and may be connected to the system 1500 so that the input port and the output port of the second vacuum motor 1502 are connected to the closed system 1500. For example, in an embodiment in which the second vacuum motor is an n=1 piston vacuum motor, the motor 1502 pulls a vacuum during the first phase and releases captured air during the second phase. Since the released air goes back into the closed system 1500, air will cause vibrations in the flange assembly 1504, thus providing the vibratory waveform, such as the waveform 1302 shown in FIG. 10B. In an alternative embodiment, the user may simply connect the input port, which will generate a stair-step curve.

Figure 19:
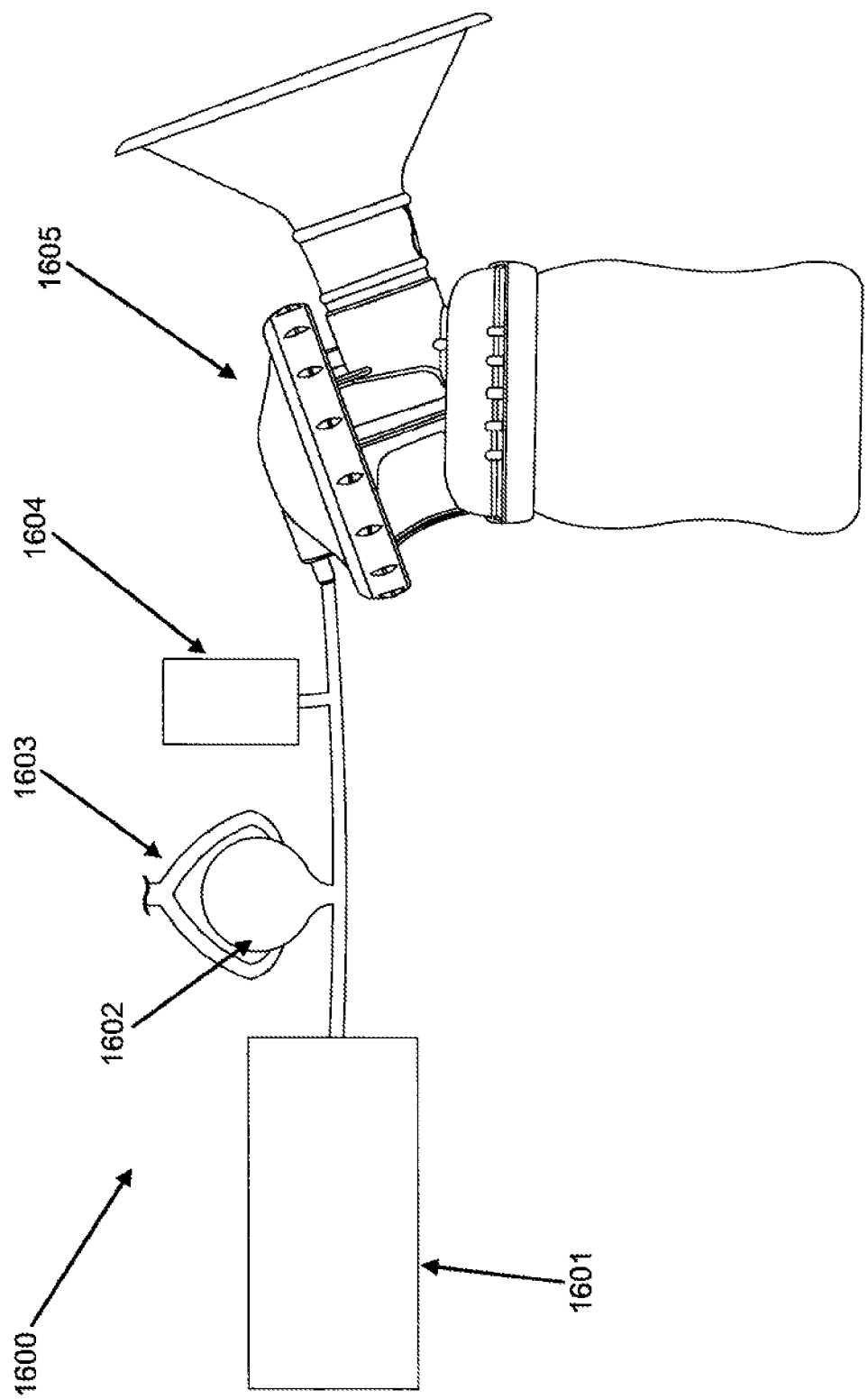
FIG. 19 is a diagrammatic view of a breast pump system that includes a bulb the motor squeezes to increase pressure in the system, according to one embodiment.

Referring to FIG. 19, another embodiment of a breast pump system 1600 is illustrated. This embodiment includes a vacuum motor 1601, a flexible bulb 1602, an external motor 1603, a solenoid 1604 and a flange assembly 1605. The vacuum motor 1601 provides the main source of vacuum for driving the breast pump system 1600 and providing suction to the flange assembly 1605. The external motor 1603 is attached to the flexible bulb 1602 (rubber bulb or similar material), and the two work together to generate the vibratory waveform. First, the external motor squeezes the bulb 1602 to expel air into the system 1600. The expelled air decreases the overall vacuum in the flange assembly 1605. When the external motor 1603 relaxes and allows the bulb 1602 to expand, air is pulled back into the valve, thus increasing the overall vacuum in the system 1600. Thus, the vibratory waveform is provided.

Although this detailed description has set forth certain embodiments and examples, the present invention extends beyond the specifically disclosed embodiments to alternative embodiments and/or uses of the invention and modifications and equivalents thereof. Thus, it is intended that the scope of the present invention should not be limited by the particular disclosed embodiments described above.

We claim:

1. A method for facilitating milk extraction from a female breast, the method comprising:

applying a breast contacting portion of a breast pump system to a breast;

activating the breast pump system to administer multiple breast pumping cycles comprising a suction pattern, wherein each of the breast pumping cycles comprises an increasing vacuum segment, during which an amount of vacuum force applied to the breast increases, and a decreasing vacuum segment, during which the amount of vacuum force applied to the breast decreases; and applying vibrations to the breast during at least a portion of each of the breast pumping cycles by applying oscillations with a mechanism located in a vacuum pump of the breast pump system, wherein the mechanism comprises a release valve that turns on and off to apply the oscillations, and wherein the vacuum pump is connected to the breast contacting portion via a connector.

2. The method of claim 1, wherein the mechanism comprises at least one hole configured to provide a change in pressure during at least the portion of each of the breast pumping cycles, and wherein applying the oscillations comprises allowing air to flow through the at least one hole in a different direction relative to a main direction in which air normally flows through the vacuum pump during the portion of each of the breast pumping cycles.

3. The method of claim 1, wherein applying the oscillations comprises allowing air to flow through the vacuum pump in a different direction relative to a main direction in which air normally flows through the vacuum pump during the portion of each of the breast pumping cycles.

4. The method of claim 1, wherein the mechanism comprises:
   a bulb attached in-line with the vacuum pump; and
   an additional mechanism that automatically squeezes the bulb to expel air into the breast pump system and releases the bulb to allow it to expand to increase the amount of vacuum force in the breast pump system, wherein the additional mechanism is selected from the group consisting of a motor and a solenoid.

5. The method of claim 1, wherein the mechanism comprises a one-way valve with a diaphragm that has one or more holes in it.

6. The method of claim 5, wherein the one-way valve further comprises a flap with an opening that exposes a portion of the diaphragm with the one or more holes.

7. The method of claim 1, wherein the mechanism comprises an additional component that generates the oscillations, and wherein the additional component is selected from the group consisting of a motor and a solenoid.

8. A method for facilitating milk extraction from a female breast, the method comprising:
   applying a breast contacting portion of a breast pump system to a breast;
   activating the breast pump system to administer multiple breast pumping cycles comprising a suction pattern, wherein each of the breast pumping cycles comprises an increasing vacuum segment, during which an amount of vacuum force applied to the breast increases, and a decreasing vacuum segment, during which the amount of vacuum force applied to the breast decreases; and
   applying vibrations to the breast during at least a portion of each of the breast pumping cycles by applying oscillations with a mechanism located in a vacuum pump of the breast pump system, wherein the mechanism comprises at least one valve within the vacuum pump that leaks air to cause the oscillations, and wherein the vacuum pump is connected to the breast contacting portion via a connector.

9. A method for facilitating milk extraction from a female breast, the method comprising:
   applying a breast contacting portion of a breast pump system to a breast;
   activating the breast pump system to administer multiple breast pumping cycles comprising a suction pattern, wherein each of the breast pumping cycles comprises an increasing vacuum segment, during which an amount of vacuum force applied to the breast increases, and a decreasing vacuum segment, during which the amount of vacuum force applied to the breast decreases;
   applying vibrations to the breast during at least a portion of each of the breast pumping cycles by applying oscillations with a mechanism located in a vacuum pump of the breast pump system, wherein the vacuum pump is connected to the breast contacting portion via a connector;
   receiving, at a controller of the breast pump system, an input from a user specifying an adjustment of a parameter of the vibrations; and
   adjusting the breast pump system according to the input to adjust the parameter.

* * * * *